(12) United States Patent
Gilbert

(10) Patent No.: US 9,039,764 B2
(45) Date of Patent: May 26, 2015

(54) ELECTROCHEMICAL COUPLING OF METALLIC BIOMATERIAL IMPLANTS FOR BIOLOGICAL EFFECT

(75) Inventor: Jeremy L. Gilbert, Fayetteville, NY (US)

(73) Assignee: Syracuse University, Syracuse, NY (US)

(*) Notice: Subject to any disclaimer, the term of this patent is extended or adjusted under 35 U.S.C. 154(b) by 1044 days.

(21) Appl. No.: 12/534,443

(22) Filed: Aug. 3, 2009

(65) Prior Publication Data

US 2011/0029080 A1 Feb. 3, 2011

(51) Int. Cl.
*A61F 2/30* (2006.01)
*A61L 31/08* (2006.01)
*A61L 31/16* (2006.01)
*A61C 8/02* (2006.01)
*A61C 8/00* (2006.01)
*A61F 2/28* (2006.01)

(52) U.S. Cl.
CPC ........... *A61F 2/30767* (2013.01); *A61C 8/0007* (2013.01); *A61C 8/0012* (2013.01); *A61F 2002/2821* (2013.01); *A61F 2002/30052* (2013.01); *A61F 2250/0043* (2013.01); *A61F 2310/00023* (2013.01); *A61F 2310/00029* (2013.01); *A61F 2310/00401* (2013.01); *A61F 2310/00425* (2013.01); *A61F 2310/00473* (2013.01); *A61L 31/086* (2013.01); *A61L 31/16* (2013.01)

(58) Field of Classification Search
USPC ......................... 623/1.38, 1.42–1.46
See application file for complete search history.

(56) References Cited

U.S. PATENT DOCUMENTS

| 8,382,823 | B2* | 2/2013 | Kim et al. | 623/1.44 |
|---|---|---|---|---|
| 2005/0192661 | A1* | 9/2005 | Griffen et al. | 623/1.15 |
| 2007/0270942 | A1* | 11/2007 | Thomas | 623/1.46 |
| 2008/0131479 | A1* | 6/2008 | Weber et al. | 424/426 |
| 2008/0161906 | A1* | 7/2008 | Atanasoska et al. | 623/1.38 |
| 2010/0279179 | A1* | 11/2010 | Farrow et al. | 429/401 |
| 2014/0030310 | A1* | 1/2014 | Bayer et al. | 424/423 |
| 2014/0093417 | A1* | 4/2014 | Liu et al. | 420/411 |

OTHER PUBLICATIONS

Xiao et al., Bone Morphogenic Protein, Aug. 20, 2007, Elsevier Inc., 362, 550-553.*

* cited by examiner

*Primary Examiner* — Suzette J Gherbi
(74) *Attorney, Agent, or Firm* — David L. Nocilly; George R. McGuire; Bond Schoeneck & King, PLLC

(57) ABSTRACT

The invention discloses a novel method of controlling the open circuit potential (OCP) of a medical implant by coupling it with small amounts of metals having a lower OCP than the implant. Coupling of Mg to less than 1% of the surface area of a titanium implant is shown to induce cathodic polarization of the titanium that inhibits cell proliferation at the surface of the implant. Mg—Ti coupling in medical devices promises to attenuate or eliminate potential complications of surgery such as peri-implantitis and bacterial infections at the site of implantation.

18 Claims, 34 Drawing Sheets

ELECTROCHEMICAL COUPLING OF METALLIC BIOMATERIAL IMPLANTS FOR BIOLOGICAL EFFECT

BACKGROUND OF THE INVENTION

1. Field of the Invention

The invention relates to medical implant devices in general and particularly to novel methods of improving the biocompatible properties of medical implants by controlling the electrochemical potential at their surface.

2. Description of Related Art

The use of biomedical implants has revolutionized surgical intervention with an ever-expanding variety of applications in orthopedic, dental medicine as well as in tissue engineering. Despite their clinical success, long-term implantation of medical devices still represents an intrusion on the chemical, physiological and mechanical structure of the human body that can lead to serious complications. In an effort to mitigate adverse reactions, titanium and titanium alloys have been widely adopted as the material of choice for medical implants because of their high strength, inert nature, low weight and outstanding corrosion resistance. Attempts to further improve biocompatibility have focused on the treatment of the surface of the implants with pharmacologically or therapeutically active agents to facilitate tissue repair. For example, orthopedic implants may comprise a range of bone grafting materials, such as demineralized human bone matrix, bovine collagen mineral composites and processed coralline hydroxyapatite, calcium sulphate scaffolds, bioactive glass scaffolds and calcium phosphate scaffolds. The inclusion of osteoinductive materials actively trigger and facilitate bone growth, for example by recruiting and promoting the differentiation of mesenchymal stem cells into osteoblasts.

Despite these improvements, implants remain prone to failure because of sub-optimal integration of the implant into the surrounding tissue, which can lead to peri-implantitis, an acute, subacute or chronic inflammation that continuously affects or opposes the intended implant function. Specifically in critical implant regions, especially with dental implants, the biologic environment and physiologic conditions is a complicating factor with a higher risk of infections due to the microbial, bacterial or fungi flora. Typical effects that may be caused by peri-implantitis of dental implants are inflammation of mucosa, loss of attached gingival, exposure of a cervical portion of the implant and loss of the surrounding bone and functional implant failures. A further significant issue is that the absence of the tooth induces spontaneously alveolar bone remodeling with resulting atrophy. Atrophy may subsequently cause more complex complications for reconstruction.

For the foregoing reasons, there is a continuing need for medical implants that mitigate adverse reactions such as peri-implantitis and bacterial infections at the site of implantation.

SUMMARY OF THE INVENTION

The application discloses methods of controlling the tissue response in the vicinity of a biomedical implant by modulating the electrochemical properties at the implant's surface.

It should be understood that this application is not limited to the embodiments disclosed in this disclosure, and it is intended to cover modifications and variations that are within the scope of those of at least ordinary skill in the field, and as defined by the claims.

In one aspect, the invention relates to a medical implant, comprising a biocompatible material coupled with a metal having a cathodic electrochemical potential, the metal being configured to induce a cathodic electrochemical potential at the surface of the implant relative to the biocompatible material in the absence of the metal.

In one aspect, the metal having a cathodic electrochemical potential may comprise one or more members of the group consisting of magnesium, iron and zinc. The metal may be disposed at the surface of the implant and may comprise less than 1% of the surface of the implant.

In one aspect, the biocompatible material comprises titanium.

In another aspect, the biocompatible material comprises an alloy such as titanium-aluminum-vanadium (Ti-6Al-4V), cobalt-chromium-molybdenum (Co—Cr—Mo), or stainless steel (316L SS).

In other aspects, the cathodic potential at the surface of the implant is configured to reduce an inflammatory response of a patient to the implant or to inhibit bacterial proliferation on the surface of the implant after insertion of the implant into a patient or to reduce or eliminate bacterial infection on the surface of the implant or to promote bone healing at a site of insertion of the implant into a bone of a patient.

In another aspect, the cathodic potential at the surface of the implant is configured to promote a gradual corrosion of the metal having a cathodic electrochemical potential after insertion of the implant into a patient.

In one aspect, the surface of the implant further comprises an agonist of bone formation. The agonist may be selected from one or more members of the group comprising osteoinductive growth factors, extracellular matrix constituents, scaffolding material, bone-specific enzymes and calcium phosphate particles. The osteoinductive growth factors may comprise a bone morphogenetic protein. The scaffolding material may also comprise osteogenesis-inducing cells.

In another aspect, the implant is a stent. The cathodic potential at the surface of the stent can be configured to inhibit restenosis after insertion of the stent into a blood vessel of a patient.

In one embodiment, the invention features a method of treating a bone lesion in a patient, comprising the steps of providing a medical implant comprising a biocompatible material coupled with a metal having a cathodic electrochemical potential, the metal being configured to induce a cathodic electrochemical potential at the surface of the implant relative to said biocompatible material without the metal, and repairing a bone defect in a patient with the implant, wherein the cathodic potential at the surface of the implant promotes bone healing at the bone defect.

The cathodic potential at the surface of the implant may induce osteogenesis at the site of the bone defect or inhibit inflammation in the vicinity of the bone defect.

The previously described embodiments have many advantages, primarily because most electrical stimulators of bone (or other) healing require some sort of battery supply or other external power source to deliver the electrical energy needed to promote healing. However, the embodied invention does not depend on any outside power sources but, rather, derives its electrical energy from the electrochemical (corrosion) reactions of the degradation (oxidation) of the metal having a cathodic electrochemical potential, for example Mg, itself Thus the implant is configured to provide the electrical energy needed to induce these processes.

The embodied technology has other advantages in that, to date, there has been no development of means to directly control the voltage of an actual implant surface relative to its surroundings. Usually voltage control has been done using electrodes implanted adjacent to devices, or no voltage control has been developed for these applications (e.g., hip or knee prostheses). There is no known orthopedic implant that has a specifically controlled voltage capability meant to enhance bone in-growth, reduce inflammation, or eliminate bacterial infection. It is particularly advantageous that in apparatus and systems of the invention the voltage control is achieved by electrochemical means.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention.

DETAILED DESCRIPTION OF THE INVENTION

Figure 1B:
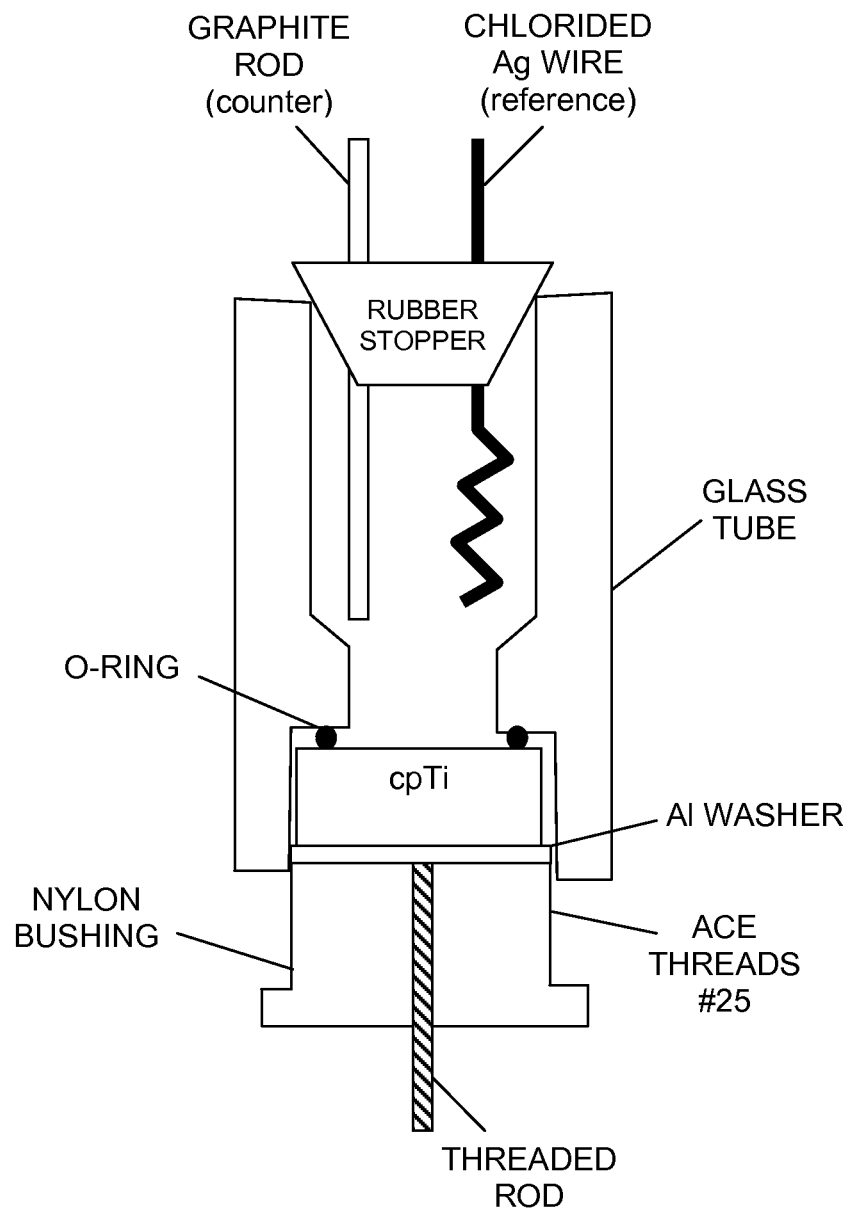
FIG. 1B schematically illustrates features of a custom designed electrochemical test chamber according to principles of the invention.
Figure 1C:
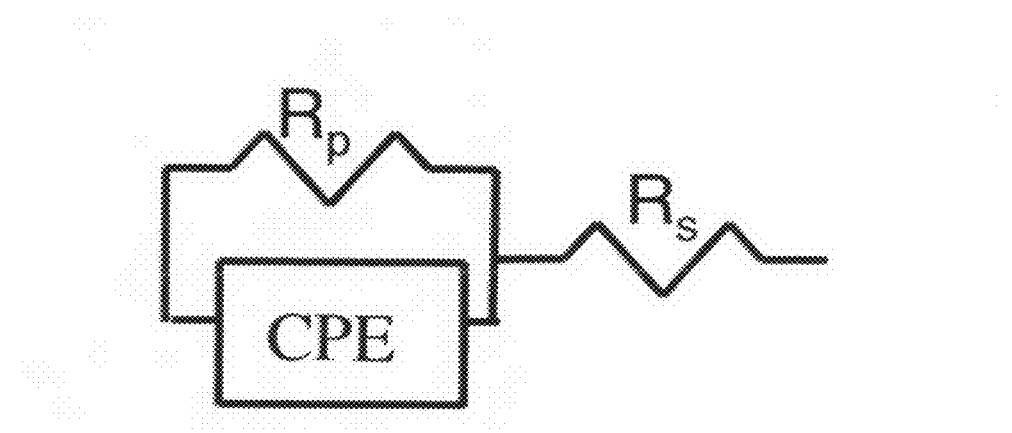
FIG. 1C illustrates a schematic of the modified Randles circuit used to model the electrochemical impedance of the cpTi interface including the solution resistance (Rs), the polarization resistance (Rp), and the constant phase element (CPE)
Figure 1D:
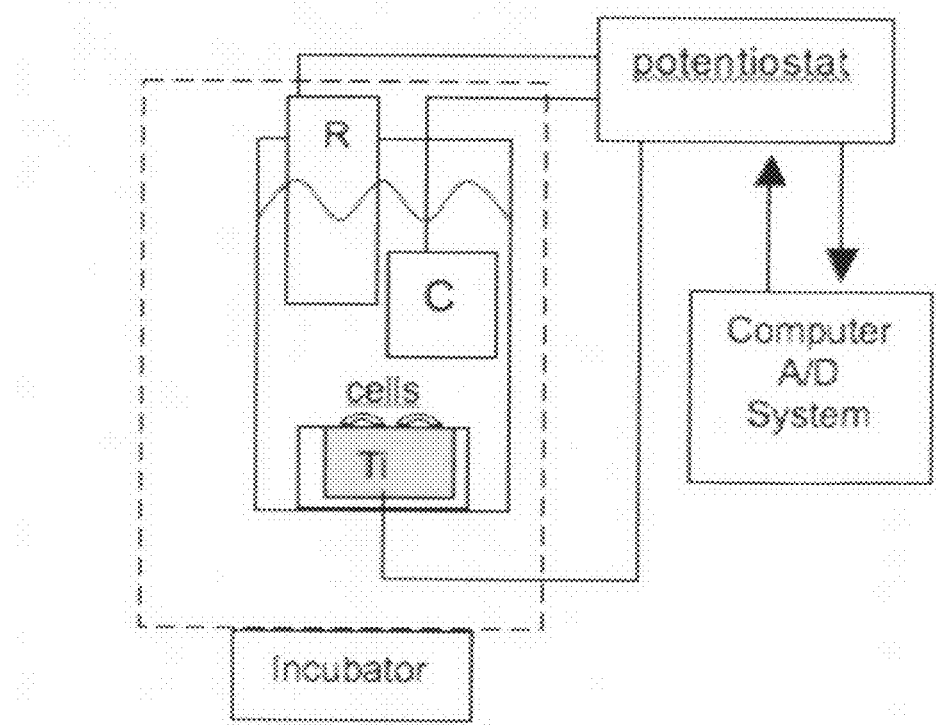
FIG. 1D shows a schematic of the cell culture set up on polished, immersed and polarized Ti.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

The term "medical device" or "medical implant", as used herein, refers broadly to any apparatus used in relation to a medical procedure. Specifically, any apparatus that comes in contact with a patient's tissues during a medical procedure or therapy is contemplated herein as a medical device. Similarly, any apparatus that administers a drug or compound to a patient during a medical procedure or therapy is contemplated herein as a medical device or implant.

In one embodiment, a "medical implant" refers to any partially or totally metallic implantable medical device that is temporarily or permanently placed in a patient. Depending on the application, implants may contain electronics e.g. implantable cardioverter defibrillators, artificial pacemakers or cochlear implants. In some instances, implants are designed to repair or totally or partially replace a tissue or an organ such as stents or artificial hearts. Implants may be bioactive, such as subcutaneous drug delivery devices in the form of implantable pills or drug-eluting stents.

In another embodiment, a medical implant refers to orthopedic bone implants that are placed over or within bones to hold a fracture reduction. For example, a medical implant includes, but is not limited to, total hip replacement systems, fracture fixation plates, intermedullary rods and nails, spinal devices, screws, or wires and the like. In certain embodiments, an orthopedic bone implant may be a prosthesis that replaces a part or whole of a defunct joint. In other embodiments, medical implants refer to dental implants that are designed to osseointegrate at their base to the bone of the mandible or maxilla and to be capped with an artificial tooth at the top of the implant.

As used herein, a biocompatible material shall be understood to mean a material that, upon implantation, falls to initiate an unacceptable biological response to an implant, for example, peri-implantitis, and is distinguished from a mild, transient inflammation and/or granulation response which can accompany implantation of most foreign objects into a living organism and is also associated with the normal healing response. Materials useful to the invention herein shall be biocompatible if, at the time of implantation, they are present in a sufficiently small concentration such that the above-defined condition is achieved. In a preferred embodiment, the biocompatible material comprises titanium or a titanium alloy.

As used herein, the term "metal", "metallic", or "metallic material" includes a pure metal or metal alloy.

As used herein, the term alloy is defined broadly such that "an alloy of metal x" encompasses alloys having any amount of x, and does not require that metal x be present as either the single most common component or that it be present at some minimum level. Thus, an alloy qualifies as "an alloy of metal x" even if metal x is present at low levels such as about 50% or less, or about 10% or less, or about 5% or less, or about 1% or less, or about 0.5% or less, or about 0.1% or less.

As used herein, a "metal" suitable for coupling with a medical implant refers to any metal whose open circuit potential (OCP) is more negative than that of a medical implant and whose coupling with a medical implant results in a cathodic potential at the surface of the implant relative to the implant in the absence of the metal. In one embodiment, coupling of the "metal" to the medical implant pulls the voltage of the system into the cathodic range, for example by at least about −0.1V, or at least about −0.2V, or at least about −0.3 V, or at least about −0.4V, or at least about −0.5V, or at least about −1 V, or at least about −1.5V or more. In another embodiment, the metal suitable for coupling to the medical implant includes, but is not limited to, Mg, Fe or Zn.

As used herein, an agonist of bone formation refers to any molecule that induces bone formation. Agonists may act directly or indirectly on osteogenic precursors to facilitate de novo bone formation.

As used herein, osteoinductive growth factors, refer to signaling proteins that act on osteogenic progenitors to produce bone. Examples of osteoinductive factors include, but are not limited to, bone morphgenetic proteins (e.g. BMP-2, BMP-3, BMP-3b, BMP-4, BMP-5, BMP-6, BMP-8, BMP-9, BMP-10, BMP-11, BMP-12, BMP-13, BMP-15), vascular endothelial growth factor (VEGF), fibroblast growth factor (FGF) and platelet-derived growth factor (PDGF). Other proteins influence bone healing in different ways. For example, transforming growth factor regulates angiogenesis, bone formation, extracellular matrix synthesis, and controls cell-mediated activities. Osteonectin, fibronectin, osteonectin, and osteocalcin promote cell attachment, facilitate cell migration, and activate cells. Other known, and useful proteins include, GDF-1, GDF-2, GDF-3, GDF-5, GDF-6, GDF-7, GDF-8, GDF-9, GDF-10, GDF-11, GDF-12, NODAL, UNIVIN, SCREW, ADMP, NURAL and osteogenically active amino acid variants thereof.

As used herein, extracellular matrix constituents refers to constituents of the organic bone matrix, including, but not limited to, collagens, cell adhesion molecules and proteoglycans.

As used herein, scaffolding material, refers to graft materials that promote osteoconduction. Osteoconduction is the physical property of the graft to serve as a scaffold for viable bone healing. Osteoconduction allows for the ingrowth of neovasculature and the infiltration of osteogenic precursor cells into the graft site. Osteoconductive properties are found in cancellous autografts and allografts, demineralized bone matrix, hydroxyapatite, collagen, and calcium phosphate.

As used herein, an osteogenesis-inducing cell is a cell that is capable of either depositing hydroxyapatite, the main component of bone, or differentiating into a cell that is capable of depositing hydroxyapatite. An "osteogenic cell" is specifically contemplated as encompassing a cell ordinarily referred to as an osteoblast or an osteocyte.

As used herein, restenosis refers to the reoccurrence of stenosis, a narrowing of a blood vessel, leading to restricted blood flow. Restenosis usually pertains to an artery or other large blood vessel that has become narrowed, received treatment to clear the blockage and subsequently become renarrowed. It can be defined as a reduction in the circumference of the lumen of 50% or more, and has a high incidence rate (25-50%) in patients who had undergone balloon angioplasty, with the majority of patients needing further angioplasty within 6 months. The risk of restenosis can be mitigated by using drug-eluting stents that are coated with pharmaceuticals that inhibit tissue growth and thus reduce the risk of restenosis from scar-tissue and cell proliferation.

As used herein, a bone defect includes any area of bone tissue that is inadequate for cosmetic or physiological purposes. Bone defects may be caused by birth defect, trauma, disease, decay, or surgery. For example, bone repair can be used to correct bone defects resulting from orthopedic, neurosurgical, plastic or reconstructive surgery, periodontal, and endodontic procedures. Specific examples bone defects include, but are not limited to, simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterial cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, and sinus lifts.

The term, "patient," as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

As used herein, a ligand refers to a binding molecule that is a member of a binding pair, i.e., two different molecules wherein one of the molecules specifically binds to the second molecule through chemical or physical means. In a preferred embodiment, binding molecules refer to antigen and antibody binding pair members. In another embodiment, binding molecules refer to one or more RNA or DNA aptamers, e.g., SELEX generated aptmers or non-SELEX generated aptamers. Other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enmes, a peptide sequence and an antibody specific for the sequence or the entire protein, polymeric acids and bases, dyes and protein binders, peptides and specific protein binders (e.g., ribonuclease, S-peptide and ribonuclease S-protein), and the like.

The term "antibody," as used herein, refers to an immunoglobulin molecule, which is able to specifically bind to one or more epitopes on an antigen. Antibodies can be intact immunoglobulins derived from natural sources or produced, e.g., by immunization, synthesis or genetic engineering (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.). Antibodies can be monoclonal antibodies, multispecific antibodies, human antibodies, humanized antibodies (fully or partially humanized), animal antibodies (such as, but not limited to, a bird (for example, a duck or goose), a shark or whale, a mammal, including a non-primate (for example, a cow, pig, camel, llama, horse, goat, rabbit, sheep, hamsters, guinea pig, cat, dog, rat, mouse, etc.) or a non-human primate (for example, a monkey, such as a cynomologous monkey, a chimpanzee, etc.), recombinant antibodies, chimeric antibodies, single-chain Fvs ("scFv"), single chain antibodies, single domain antibodies, diabodies, Fab fragments, F(ab') fragments, F(ab')2 fragments, disulfide-linked Fvs ("sdFv"), and anti-idiotypic ("anti-Id") antibodies (including, for example, anti-Id antibodies to antibodies of the present application), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG1, IgG2, IgG3, IgG4, IgA1 and IgA2) or subclass.

A "recombinant antibody" as used herein, is an antibody, which is generated using recombinant DNA technology, such as, for example, an antibody expressed by a bacteriophage as described herein. The term should also be construed to mean an antibody which has been generated by the synthesis of a DNA molecule encoding the antibody or parts thereof and which DNA molecule expresses an antibody protein or parts thereof, or an amino acid sequence specifying the antibody, wherein the DNA or amino acid sequence has been obtained using synthetic DNA or amino acid sequence technology which is available and well known in the art. Recombinant antibodies may be selected for increased or improved affinity via the screening of a combinatory antibody library under stringent binding conditions. For example, nucleic acids encoding achimeric or humanized chain can be expressed to produce a contiguous protein. See, e.g., Cabilly et al., U.S. Pat. No. 4,816,567; Cabilly et al., European Patent No. 0 125 023 B1; Boss et al., U.S. Pat. No. 4,816,397; Boss et al., European Patent No. 0 120 694 B1; Neuberger et al., International Publication No. WO86/01533; Neuberger et al., European Patent No. 0 194 276 B1; issued to Winter et al., U.S. Pat. No. 5,225,539; issued to Winter et al., European Patent No. 0 239 400 B1; Queen et al., European Patent No. 0 451 216 B1; and Padlan et al., EP 0 519 596 A1. See also, Newman et al., BioTechnology, 10: 1455-1460 (1992), regarding primatized antibody, and Ladner et al., U.S. Pat. No. 4,946,778 and Bird et al., Science, 242:423-426 (1988)) regarding single chain antibodies. The contents of these patent documents and references are hereby incorporated herein in their entirety.

The following description relates to certain preferred embodiments of the application, and to a particular methodology for the modulation of the electrochemical properties of an implant device. As will be readily apparent from the discussion, the inventive concepts described herein can also be suitably applied to any medical implant.

Electrochemically-based reactions play a fundamental role in all biological systems. For example, generation of energy sources, use of energy sources, synthesis of proteins and enzymes are all redox-based processes. Cell membrane constituents such as voltage-sensitive membrane channels or nuclear pores are susceptible to electrochemical potentials and protein conformation can be altered by redox reactions. Hence, when cells come into contact with, attach and grow on metallic implants, their basic life processes can be significantly affected by the redox reactions (also known as Faradaic reactions) that may be present at the surface of implant. Recent studies indicate such charge transfer processes (i.e., currents that transit the metal-oxide-solution interface) can be significantly altered in many metallic devices by mechanical abrasion. Also, various biological molecules can engage in Faradaic (charge transfer) reactions when they are in proximity to a surface capable of undergoing charge transfer reactions. Many biological species (e.g., proteins, inflammatory species like reactive oxygen) are susceptible to redox (electrochemical) reactions. Whereas mechanobiology, nano-topographic effects, and chemical modification of biomaterial surfaces have all been identified and explored as potent control stimuli of cell-material and protein-material interactions, one area that has received less attention is the electrical and electrochemical factors (both charge accumulating effects and charge transfer effects) that impact protein adsorption and cell-surface interactions.

The invention describes how the voltage on the surface of an implant device can vary significantly depending on the mechanical and electrochemical environment of the device. By inducing changes in the surface voltage of the implant, it is possible to alter various important biological processes; for example, those associated with osseointegration, wound healing and bacterial infection.

The ability to control the surface voltage of metallic orthopedic devices may assist in and control aspects of the healing process that will improve healing rates and extent. More specifically, surface voltage of implants may affect: 1) bone healing in ways similar to direct current (DC) electrical stimulators used in non-union healing; 2) inflammatory processes in species such as hydrogen peroxide by electrochemically reducing these oxidizing agents under appropriate voltage conditions; and 3) biomaterial-centered bacterial infection by promoting and enhancing local antibiotic penetration into biofilms on metallic surfaces.

Control of Bone-Like Cell Behavior on Polarized Commercially Pure Titanium and the Effect of Voltage on Current Densities and Impedance Characteristics.

An electrochemical cell culture system (See FIGS. 1A-1E) was designed which allowed for maintenance of sterile conditions and the culturing of cells on metal surfaces, while also being able to apply and measure potential, current, and surface electrochemical impedance simultaneously. The Ti sample sits at the bottom and the counter and reference electrodes are introduced through the top. Cells are plated onto the Ti surface, the chamber filled with medium and the entire assembly is placed into an incubator at 37° C. and 5% $CO_2$.

Chamber Prep

Discs of grade 4, commercially pure titanium (cpTi, Allvac) were prepared through sequential wet sanding to a 600 grit finish. The samples were then rinsed in deionized water, ultrasonically cleaned in deionized water for 10 mins, rinsed in 70% ethanol, and then exposed to UV light for 60 mins for sterilization. The samples were then mounted in the bottom of a custom glass electrochemical cell culture chamber (FIG. 1B). As shown in FIG. 1B, a threaded rod was connected to the underside of the cpTi and passed through the threaded nylon bushing to provide external electrical contact to the cpTi sample. When the glass chamber was threaded on to the nylon bushing an o-ring was compressed providing a water tight seal around the cpTi surface. This set-up exposed 3.8 $cm^2$ of the cpTi sample to the interior of the chamber. The chamber was sealed at the top end with a rubber stopper with access holes for gas exchange, graphite rod counter electrodes, and a chlorided silver wire reference electrode. The cpTi sample served as the working electrode.

Cell Culture

In all experiments the MC3T3-E1, subclone 4, pre-osteoblast cell line (ATCC #: CLR-2593) was cultured in the Alpha Modification of Eagle's Medium (AMEM, Cellgro) supplemented with 10% (v/v) fetal bovine serum (FBS, Gibco), 1% (v/v) penicillin/streptomycin (Gibco), and 1% (v/v) L-glutamine (Gibco). Cells were initially grown to near confluence in T-75 culture flasks. The culture media was aspirated and the flasks were rinsed in phosphate buffered saline (PBS, Gibco) to remove unattached cells. Next, the attached cells were enzymatically freed from the flask with the addition of 1 mL trypsin/edta (Gibco). The cells were then counted with a hemocytometer to achieve the appropriate cell seeding concentration. The 24 hr cell spreading and viability experiments were seeded with 50,000 cells in 1 mL of medium, while the 72 hr proliferation experiments were seeded with 20,000 cells in 1 mL of medium to allow for more cell growth. These 1 mL cell suspensions were slowly dispensed onto the cpTi surface and allowed to settle for 30 mins. Then, an additional 14 mL of medium was slowly added to immerse the counter and reference electrodes. The chamber was then placed in the incubator and electrode connections were made to a potentiostat (EG&G 263, Princeton Applied Research).

Electrochemical Testing

The cpTi samples were potentiostatically held at either −1000 mV, −600 mV, −300 mV, 0 mV, +300 mV, +600 mV, +1000 mV or allowed to sit at OCP. All voltages in this study are with respect to a chlorided silver wire reference electrode (Ag/AgCl). At specified time points during the experiment (0, 24, 72 hrs) the electrochemical impedance of the interface was determined with PSIA. Briefly, the static PSIA test consisted of initially holding the cpTi at the desired voltage and at a specified time delivering a 50 mV step in potential to the sample. The current transient response was subsequently analyzed with a time and frequency domain technique to determine the values of the modified Randles circuit elements (FIG. 1C) that are used to model the impedance of the cpTi interface. Specifically, the solution resistance ($R_s$), polarization resistance ($R_p$), capacitance (C), and CPE exponent, alpha, are calculated with PSIA. After PSIA testing the cpTi samples were returned to their respective static potentials until the next test time point.

Cell Morphology

After 24 hrs in culture the cpTi samples were rinsed with PBS to remove non-adherent cells. The adherent cells were then fixed with 4% formaldehyde for 2 hrs in the refrigerator and then dehydrated using graded ethanol mixtures up to 100% ethanol. The epTi samples were freeze-dried and sputter coated for scanning electron microscopy (SEM). Images of the surface were captured at fixed magnifications in both the secondary electron (SE) and backscattered electron (BSE) mode. The variation in brightness/darkness in BSE images corresponds to compositional variations at the surface. The SE images capture the topographical features of the surface. The captured images were assessed both qualitatively and quantitatively. The qualitative assessment was comprised of a general characterization of cell morphology and noting interesting features that stood out. In the quantitative assessment the SEM images were exported to ImagePro image analysis software for determination of the average projected area per cell. It was assumed that the cells were ellipses and therefore the projected area of each cell could be determined by measuring the major and minor axis of a cell. A total of 140 cells were measured for every voltage examined.

Cell Viability and Proliferation

Cell viability was determined with an MTT [3-(4,5-dimethlythiazol-2-ly)-2,5-diphenyltetrazolium bromide] assay (Gibco). After specified incubation periods (24 & 72 hrs), the electrodes were disconnected from the potentiostats and the culture medium was aspirated. Then 2 mL of fresh medium was added to the chambers along with 1% v/v of MTT solution (5 mg/mL). The chambers were then placed back in the incubator for an additional 2 hrs without electrical polarization. During this time, metabolically viable cells cleaved the tetrazolium rings of the MTT solution to produce formazan crystals within the cell. After 2 hours of incubation, the medium was aspirated and the cell monolayer was lysed with 500 µL of dimethyl sulfoxide (Sigma). The optical density ($OD_{570}$) of the resultant lysate was measured at a wavelength of 570 nm with a microplate reader. The $OD_{570}$ was corrected for background absorbance by running control MTT experiments for epTi incubated with only culture medium and no cells. MTT assay calibration was performed by comparing outcomes of parallel MTT ($OD_{570}$) and direct cell counting (cell number) experiments. The $OD_{570}$ results can be used to compare relative differences in viability between voltages and can also be used to track relative rates of cell proliferation. Positive control experiments were conducted in 12 well tissue culture plates (TCP) plates with identical cell seeding density/surface area for each experiment. The corrected $OD_{570}$ of the experimental cpTi samples are reported as a percentage of the control TCP results.

Statistical Analysis

Three cpTi samples were tested at each voltage for each cell culture measurable outcome. The impedance outcomes were combined to give a total of 6 impedance measurements per voltage. The projected cell area, $OD_{570}$, and the PSIA impedance outcomes ($R_p$, C, alpha, current density) at 24 hrs were compared across voltage through one way ANOVA (p=0.05) followed by Tukey's post-hoc analysis. The PSIA impedance outcomes ($R_p$, C, alpha, current density) for each enforced voltage were also compared across time with student t-tests. All statistical calculations were performed using SPSS statistical software.

Using this experimental system, the cell response to a wide range of electrochemical conditions could be monitored from a cathodic potential and reduction currents passing the interface, to anodic potentials, where oxidation currents are present. These potentials can be maintained for prolonged periods (72 hrs was the longest experiment performed to date). After some period of time of cell culture, the metal surfaces with the cells were rinsed, the cells were then fixed and imaged using either a scanning electron microscope or optically to observe cellular structures and behavior. Also, a biochemical assay that measures the number of viable cells in a culture system was performed (an MTT assay, which is a spectroscopic method of determining how many cells are alive). In the MTT experiment, the potentiostatic control was stopped when subjecting the cell culture to the assay since the reactions involved are based on electrochemical reactions in the mitochondria. At sufficient cathodic potential the assay would show a false positive results because of the reaction of the chemistry by the Ti surface alone.

Figure 2:
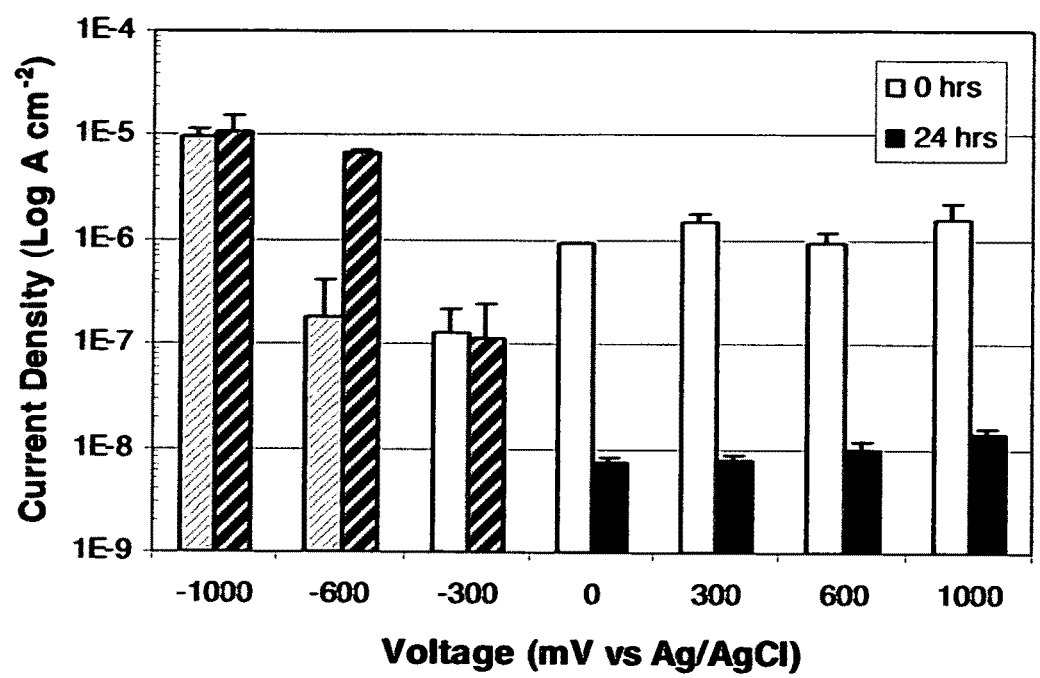
FIG. 2 shows a plot of the initial current measured for each voltage prior to the PSIA testing at 0 (grey) and 24 (black) hours.

The static current density values at 0 and 24 hrs are plotted in the FIG. 2. The columns represent the average of 3 samples with error bars of 1 standard deviation. The solid columns indicate anodic current densities while the cathodic current densities are indicated with the diagonal slashes. At 0 hrs the current density was anodic in the potential range of −300 mV to +1000 mV and the current density was cathodic at −600 mV and −1000 mV. At 24 hrs the −300 mV current density switched from anodic to cathodic but the current density orientation remained constant at all other potentials. The transition in the current density at −300 mV fit with the trend in the OCP. Initially the OCP was −500 mV and after 24 hrs the OCP shifted to −190 mV. It is also noted that the anodic current density decreased by 2 orders of magnitude in the potential range of 0 mV to +1000 mV while the cathodic current density at −600 mV increased by greater than 1 order of magnitude over the 24 hr experiment.

Figure 3:
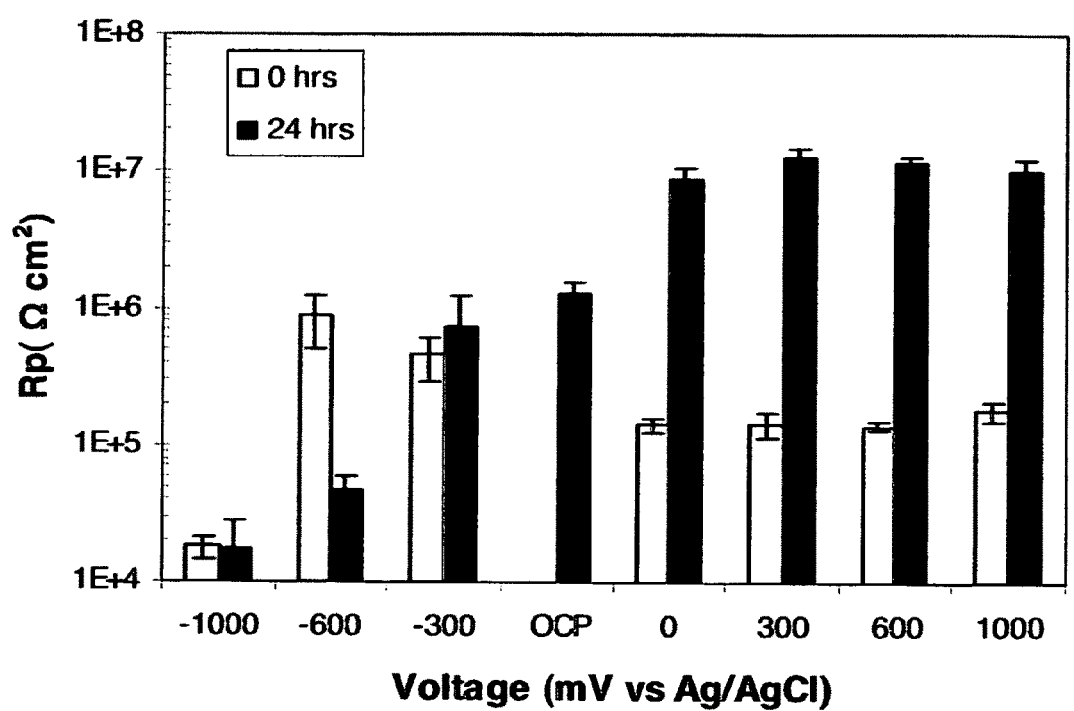
FIG. 3 shows a plot of the polarization resistance calculated for each voltage with PSIA testing at 0 and 24 hrs.

FIG. 3 displays the $R_p$ values across the voltage range investigated at 0 hrs and 24 hrs of incubation. PSIA tests were only conducted at 24 hrs for OCP. The data represent the average of 3 samples with error bars of 1 standard deviation. It was apparent that after 24 hrs of incubation there were significant changes in the $R_p$ for most applied potentials. Specifically, between 0 mV and +1000 mV the 24 hr $R_p$ values increased by about 2 orders of magnitude as compared to the 0 hr values. From 0 mV to −1000 mV, the 24 hr $R_p$ decreased in an approximate log-linear fashion from $10^7$ Ω-cm$^2$ at 0 mV to approximately $10^4$ Ω-cm$^2$ at −1000 mV. It was also noted that the $R_p$ decreased during the 24 hr incubation at −600 mV. The main observation here was that the $R_p$ of cpTi decreased systematically with potential from 0 mV to −1000 mV after 24 hrs of immersion in all solutions. This lowering of $R_p$ with voltage effectively makes the interface less corrosion resistant compared to anodic potentials.

Figure 4A:
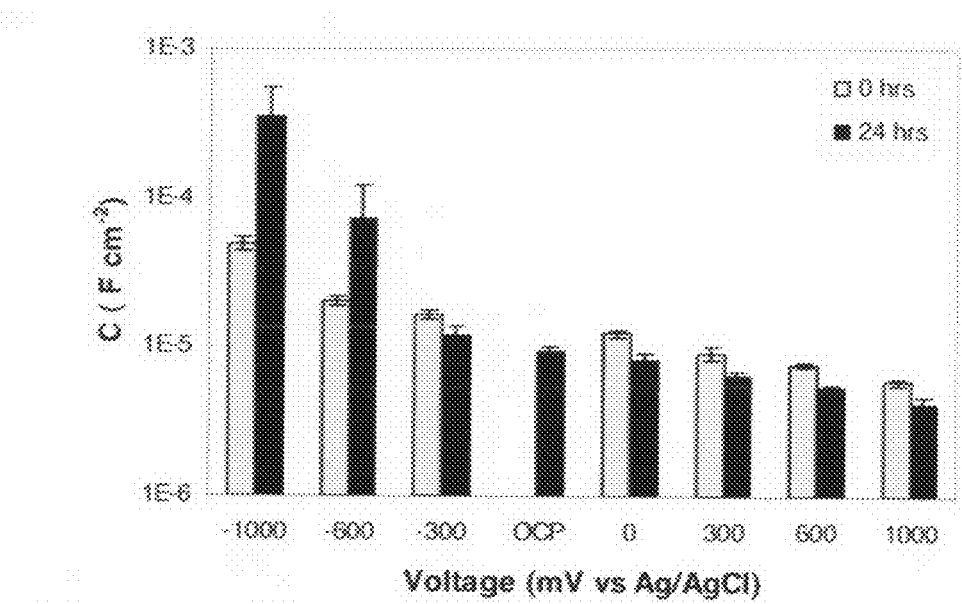
FIG. 4A shows a plot of the capacitance calculated for each voltage with PSIA testing at 0 and 24 hrs.
Figure 4B:
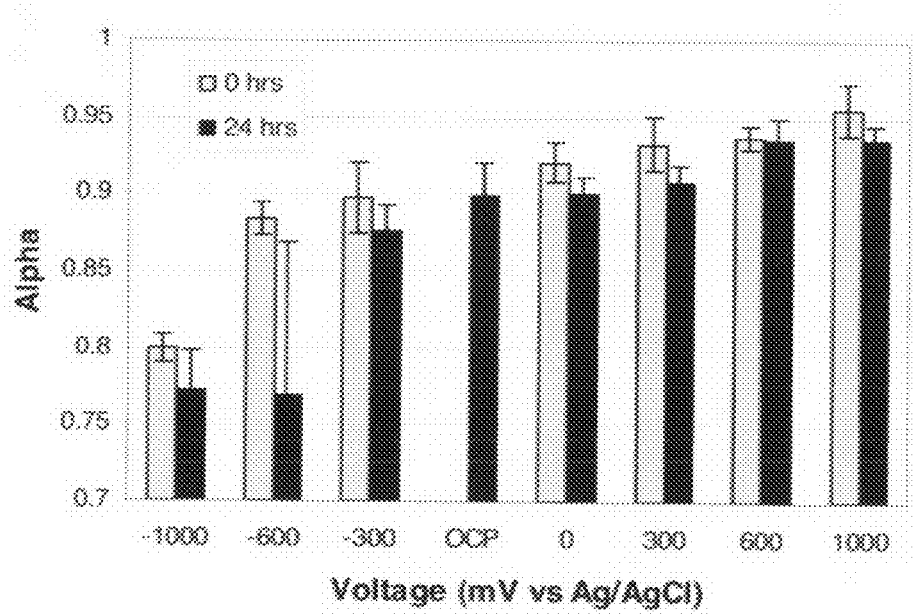
FIG. 4B shows a plot of the CPE exponent, alpha, calculated for each voltage with PSIA testing at 0 and 24 hrs.

FIG. 4A illustrates that the capacitance (C) was dependent on voltage at both 0 and 24 hrs. PSIA tests were only conducted at 24 hrs for OCP. The columns represent the average of 3 samples with error bars of 1 standard deviation. At either time point the C decreased with increasingly anodic voltage. It was father noted that the C decreased over 24 hrs in the potential range of 0 mV to +1000 mV, while it increased at −600 mV and −1000 mV. FIG. 4B indicates that the CPE exponent, alpha, generally increased from −1000 mV to +1000 mV for both the 0 hr and 24 hr results.

Figure 5:
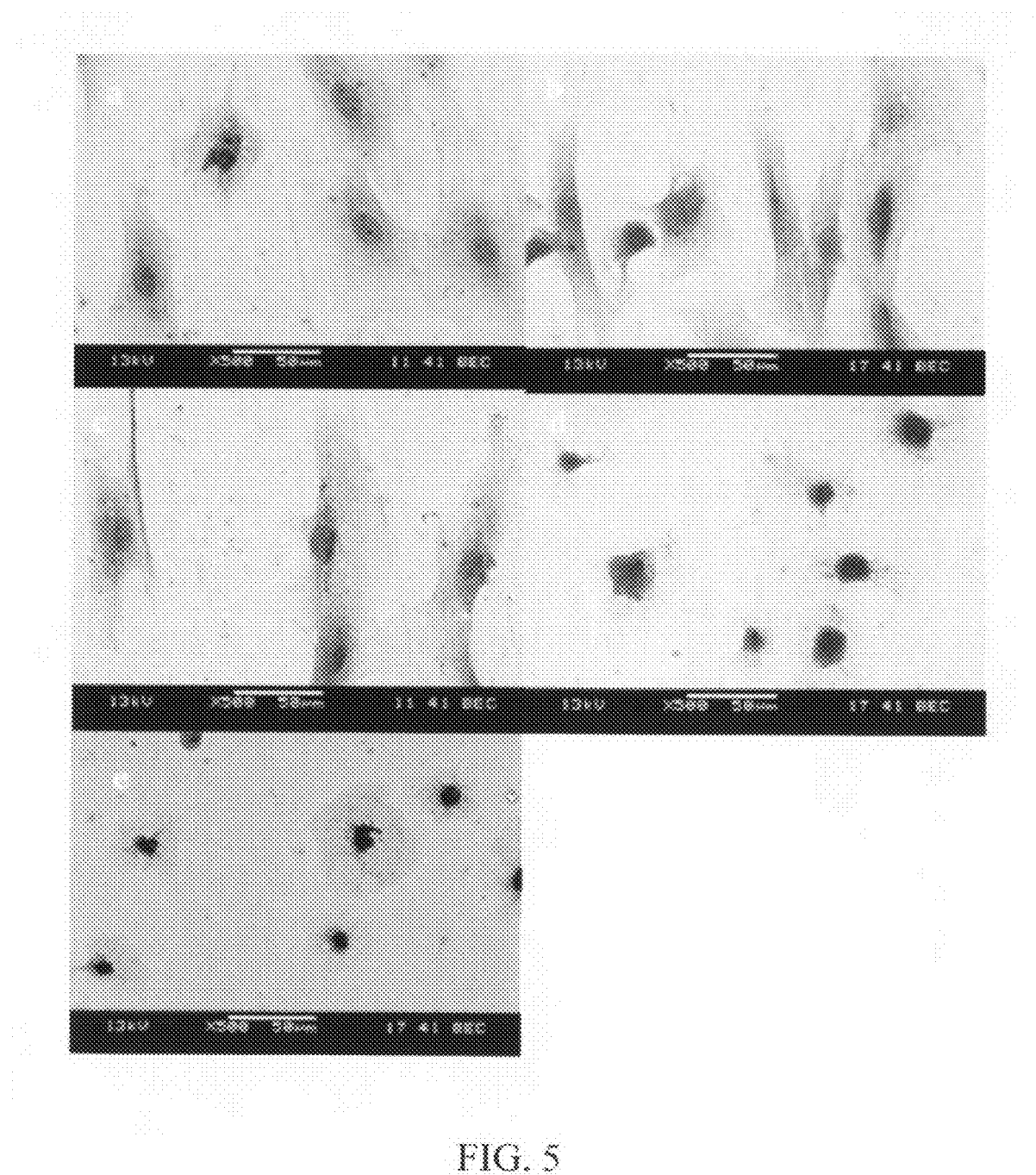
FIG. 5 shows backscattered electron micrographs of MC3T3 cells cultured on polarization Cp-Ti at a) 1000 mV, b) 0 mV, c) −300 mV, d) −600 mV, and e) −1000 mV.
Figure 6:
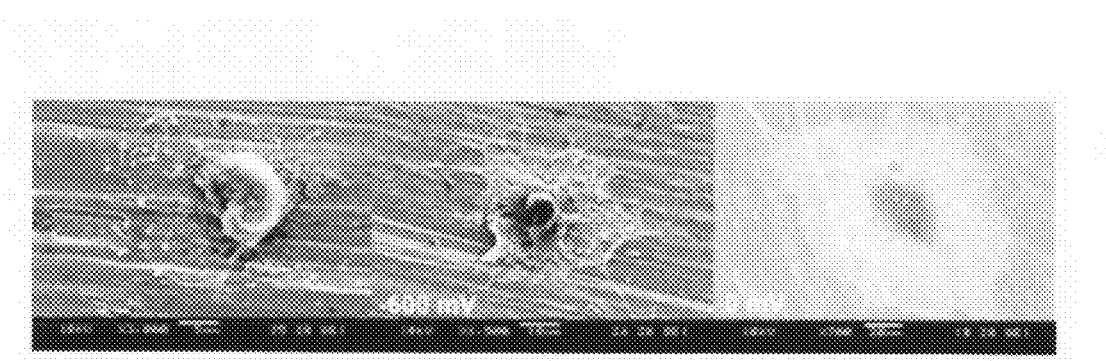
FIG. 6 shows SEM micrographs (secondary electron imaging) of MC3T3-E1 pre-osteoblast cells cultured in CpTi surfaces held at various potentials (vs Ag/AgCl) for 24 hrs.
Figure 7:
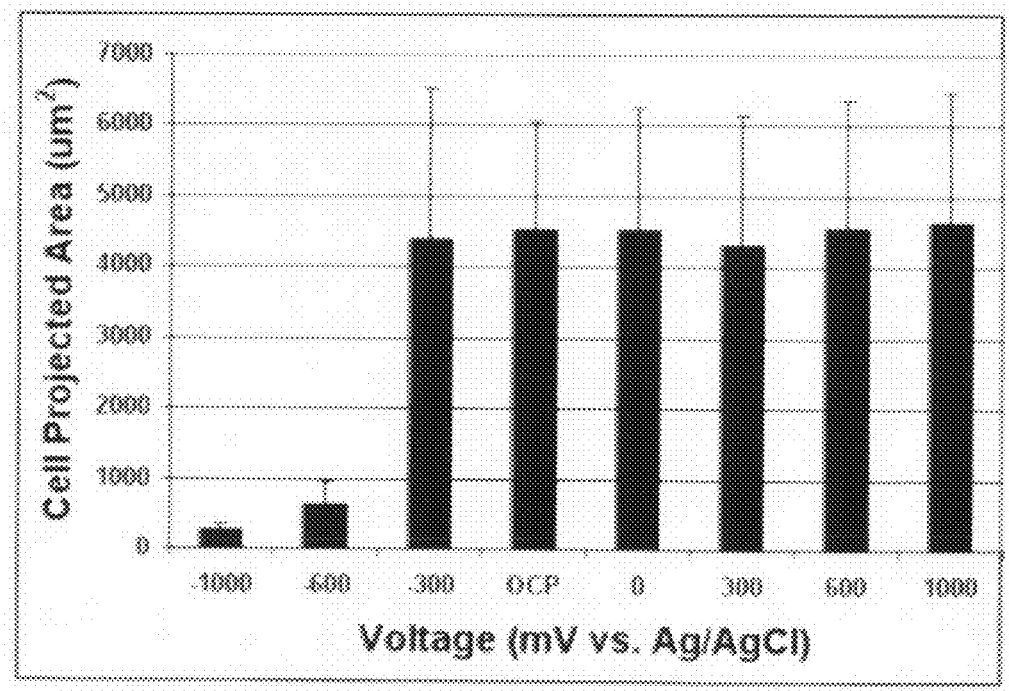
FIG. 7 depicts projected cell area versus applied potential after 24 hours of polarization.
Figure 8:
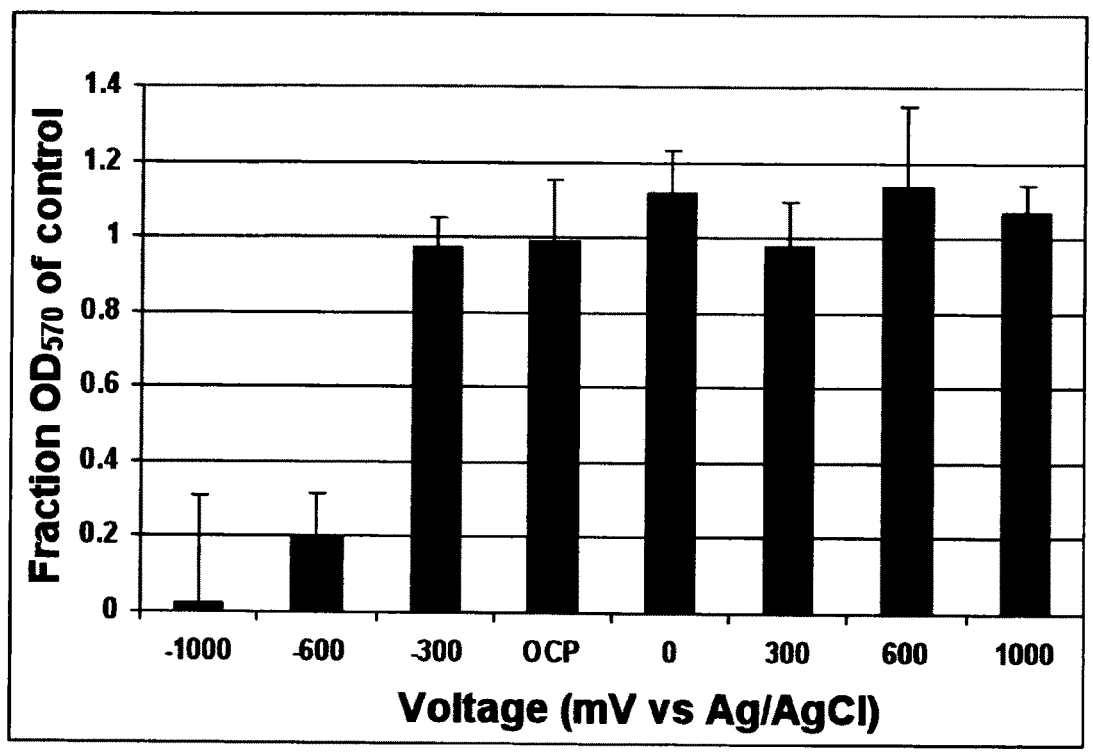
FIG. 8 illustrates MTT results for cells after 24 hours of cell culture under polarized conditions.

Examples of the cell morphology on these surfaces are summarized in FIGS. 5 and 6, which show the cell shapes after 24 hr cultures. For voltages between −300 mV and +1000 mV, the cells exhibited similar shape, size and viability. Cells were well spread, their nuclei were flat and the cytoskeleton and intracellular organelles are observable in backscattered electron imaging. The nucleoli are also evident in these images. However, when the potential dropped below −300 mV to −600 mV, the cell shapes and viability were dramatically altered (see FIGS. 2 and 3). The projected cell area was determined from the micrographs and the cell viability was measured using an MTT assay, which assesses mitochondrial activity with a chromometric analysis. The projected cell area is significantly reduced compared to the more positive potential, and the nuclei are more rounded and opaque to backscattered electrons. Projected cell area is shown in FIG. 7 and cell viability is shown in FIG. 8 after 24 hours of potentiostatic hold. Cell area and viability closely tracked one-another with viability decreasing 80% at 600 mV and almost 90% at −1000 mV when compared to cells cultured at −300 mV or higher. MTT assay results confirmed the SEM analysis in that the cell viability dropped precipitously at −600 mV and more negative voltages compared to the other potentials. There is therefore a strong inverse correlation between cathodic current density and cell area and viability and the voltage dependent change in polarization resistance. This latter observation indicates that the voltage of the interface can dramatically alter the resistance of the interface to corrosion reactions.

The results of the 24 hr experiments were evaluated to determine which potentials should be used for the 72 hr proliferation experiments. The potentials selected were OCP, −300 mV, 0 mV, and +1000 mV. The logic used here was that those potentials at which the cells displayed poor outcomes at 24 hrs, such as −600 mV and −1000 mV, would not be used for the longer experiments. Of the remaining potentials that displayed good viability at 24 hrs, the OCP condition was selected in order to establish the proliferation outcomes for cpTi without the influence of enforced potentials. The 24 hr electrochemical results for −300 mV revealed it had the lowest $R_p$, highest C, and lowest alpha of all the other potentials with good viability at 24 hrs. In addition, −300 mV was the only condition which displayed good cell viability in the presence of cathodic current density. The 0 mV and +1000 mV conditions were selected for the long term experiments because they spanned the anodic range of potentials which at 24 hrs all had the same electrochemical properties and cell morphology and viability.

Figure 9:
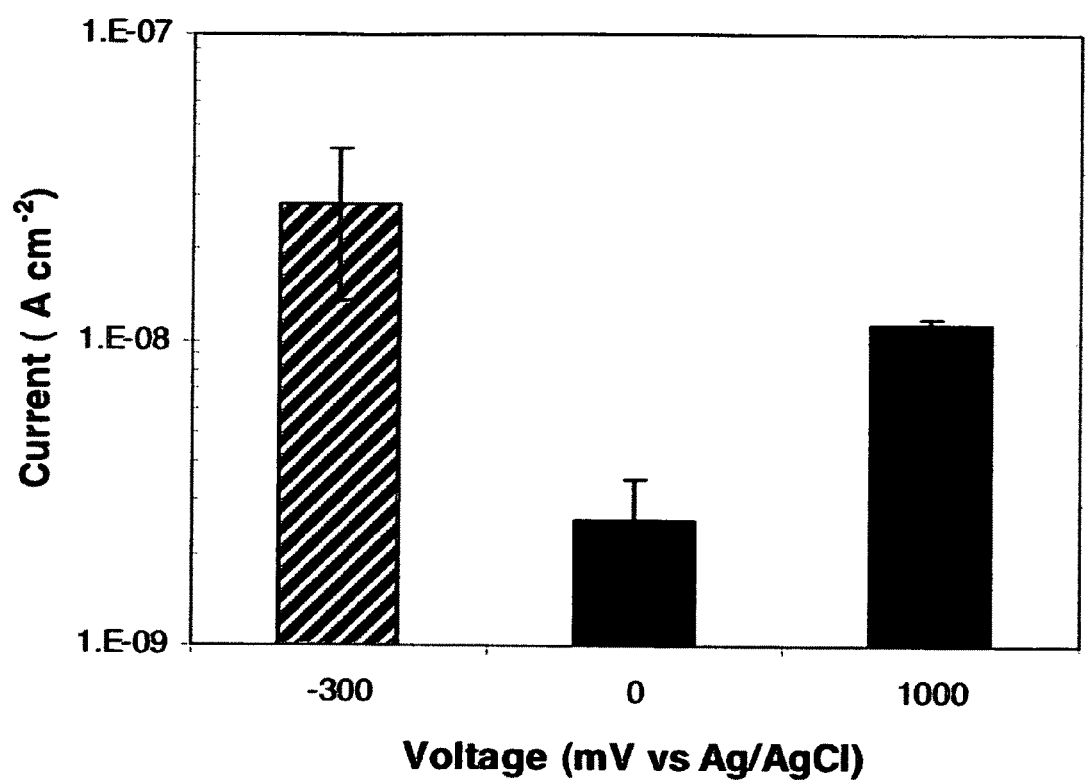
FIG. 9 shows a plot of the initial current densities measured for each voltage prior to the PSIA testing at 72 hrs.
Figure 10:
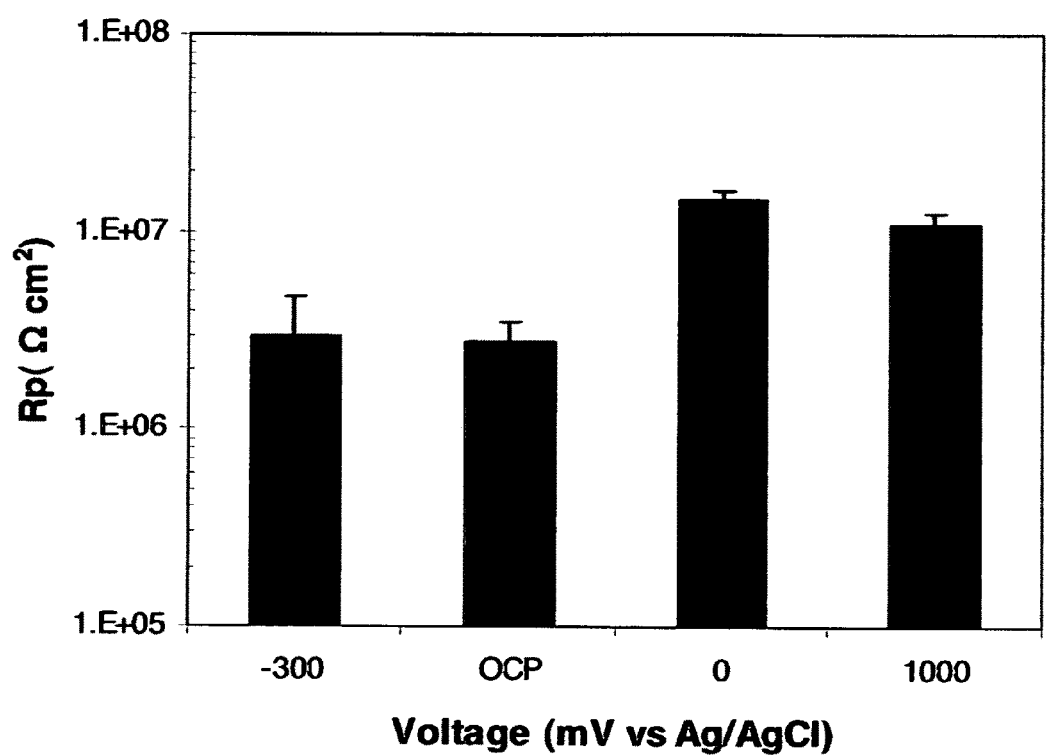
FIG. 10 shows a plot of the Rp calculated for each voltage with PSIA testing at 72 hrs.
Figure 11:
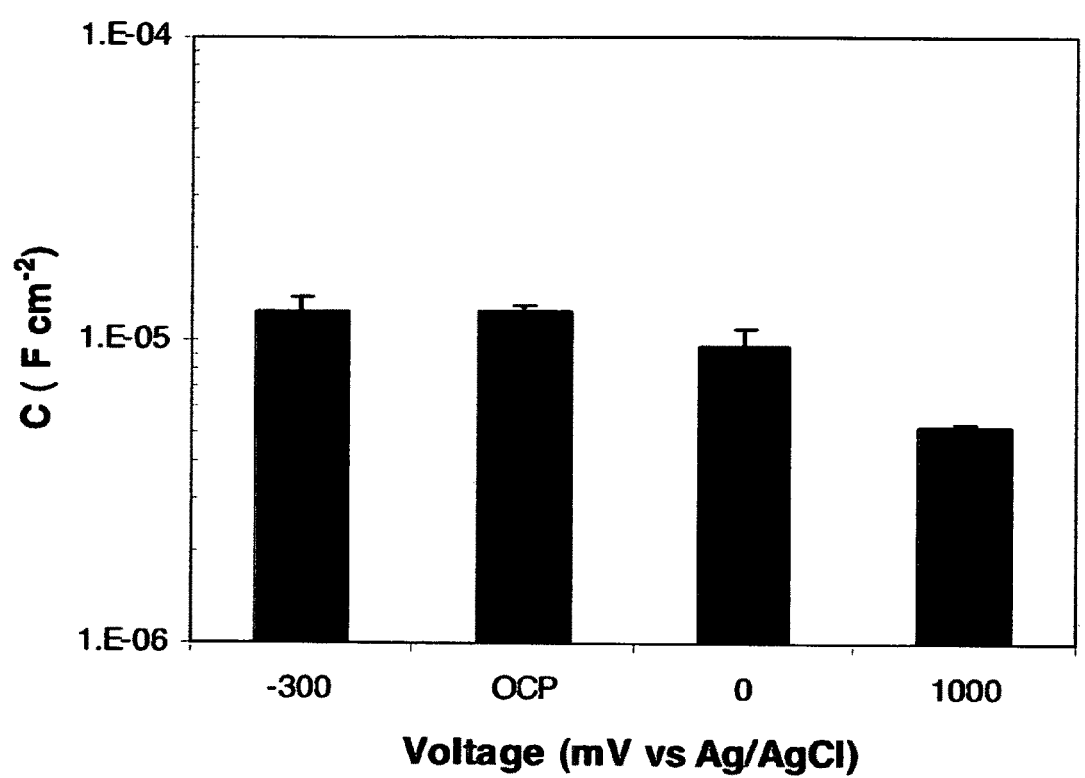
FIG. 11 shows a plot of the capacitance calculated for each voltage with PSIA testing at 72 hrs.
Figure 12:
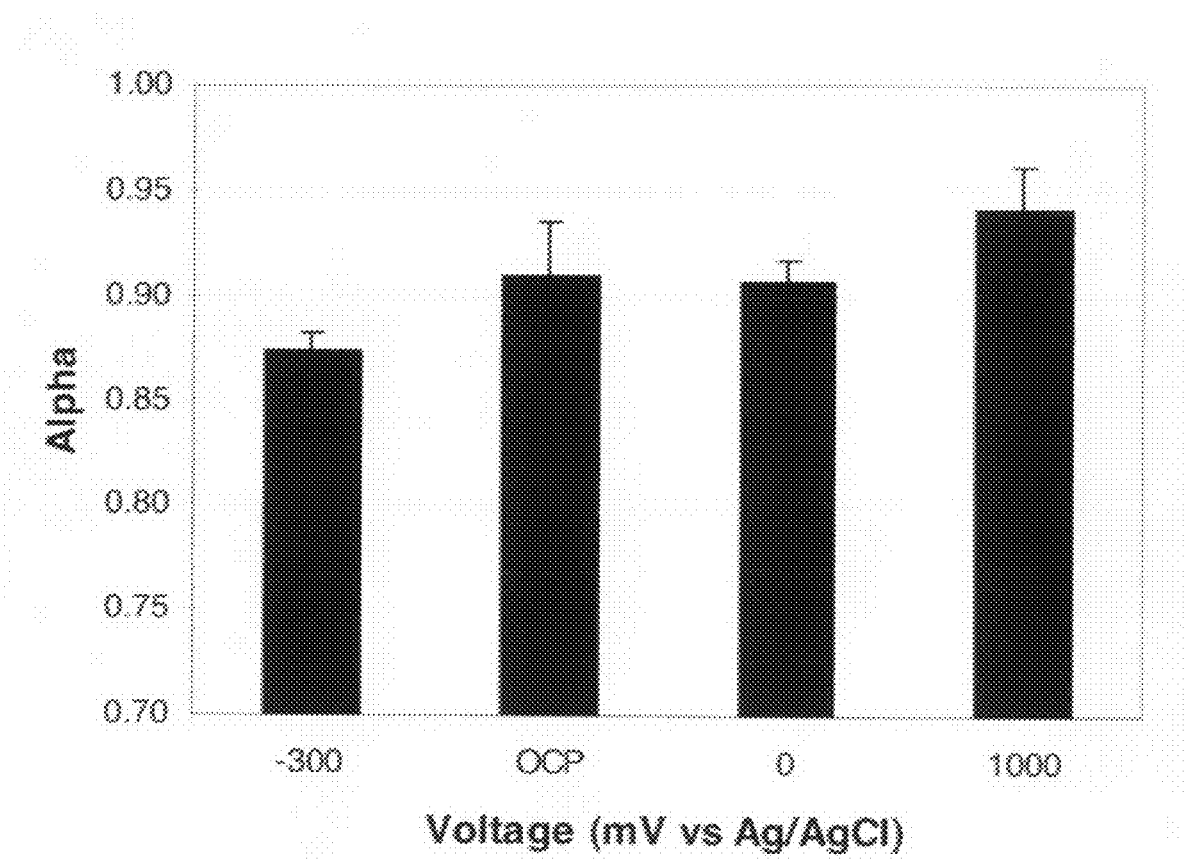
FIG. 12 shows a plot of the CPE exponent, alpha, calculated for each voltage with PSIA tests at 72 hrs.
Figure 13:
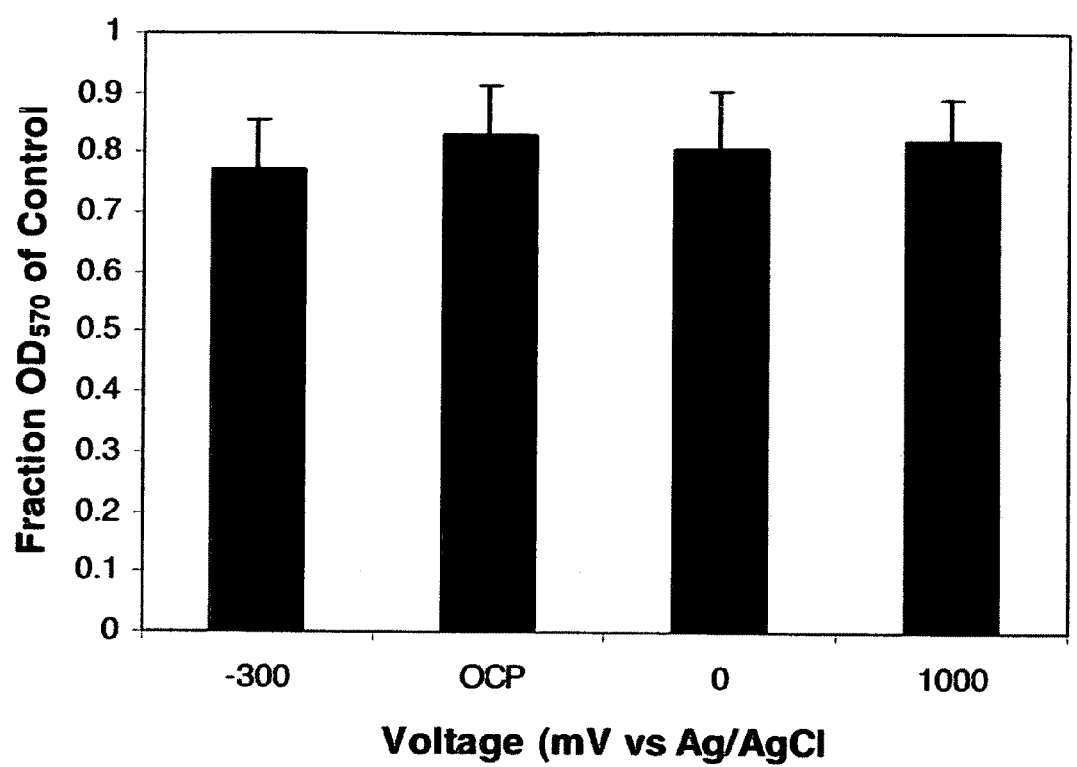
FIG. 13 shows a plot of the 72 hr MTT assay outcomes for each potential.

The 72 hrs current density values (FIG. 9) were significantly different at all potentials tested. FIG. 10 displays the $R_p$ values across the voltage range investigated at 72 hrs of incubation. The $R_p$ at −300 mV and OCP were not different from each other, but are both significantly lower than either 0 mV or +1000 mV. FIG. 11 displays that the 72 hr capacitance (C) significantly decreased with increasingly anodic voltage and FIG. 12 displays that the CPE exponent, alpha, significantly increased with anodic voltage. The 72 hr MTT assay outcomes (FIG. 13) reveals that there were no differences noted in cell proliferation in the potential range of −300 mV to +1000 mV.

The electrochemical character of the Ti surface correlated very well with the cellular response to these surfaces. This can be seen in FIG. 14 which shows the average current density crossing the Ti-electrode surface as a function of voltage (FIG. 14A) as well as the variation in polarization resistance (Rp), FIG. 14B, with overlaying plots of cell area and cell viability (MTT results). Note that the cathodic (negative, or reduction) current densities rise and remain above 100 ηA/cm2 for voltages more negative than −300 mV and this seems to be a threshold value. Interestingly, at the positive potentials, the current densities were anodic, but never exceeded this threshold current density so it is not known if anodic current densities of this magnitude will induce similar effects. Cathodic potentials, however, are known to disrupt proteins, consume local oxygen, and may affect the redox systems inside the cells that are cultured directly on the surface and that they have induced the observed effects.

Figure 14A:
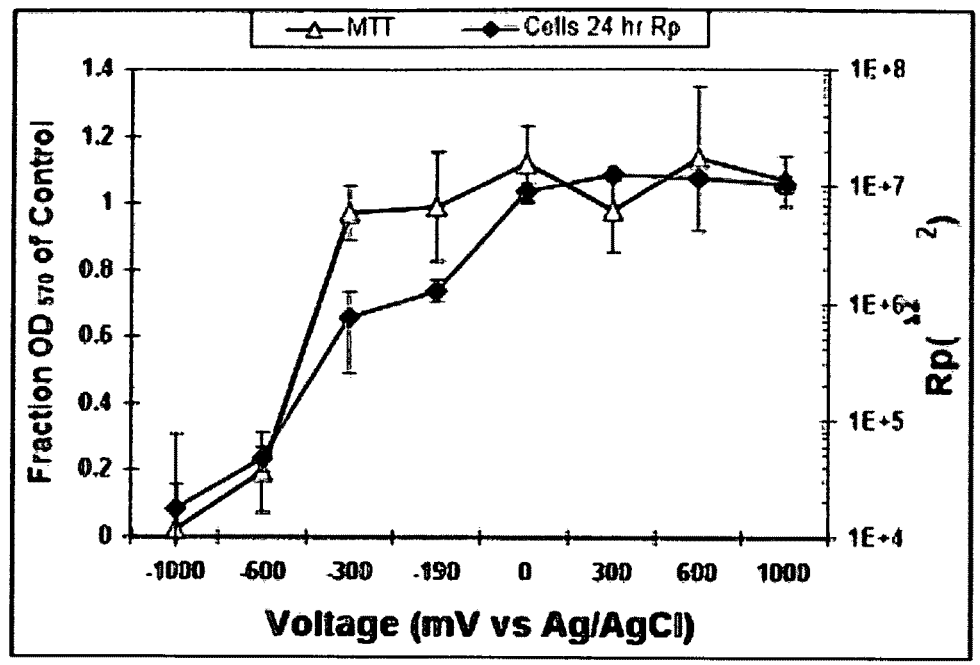
FIG. 14A depicts current density and projected cell area versus potential.
Figure 14B:
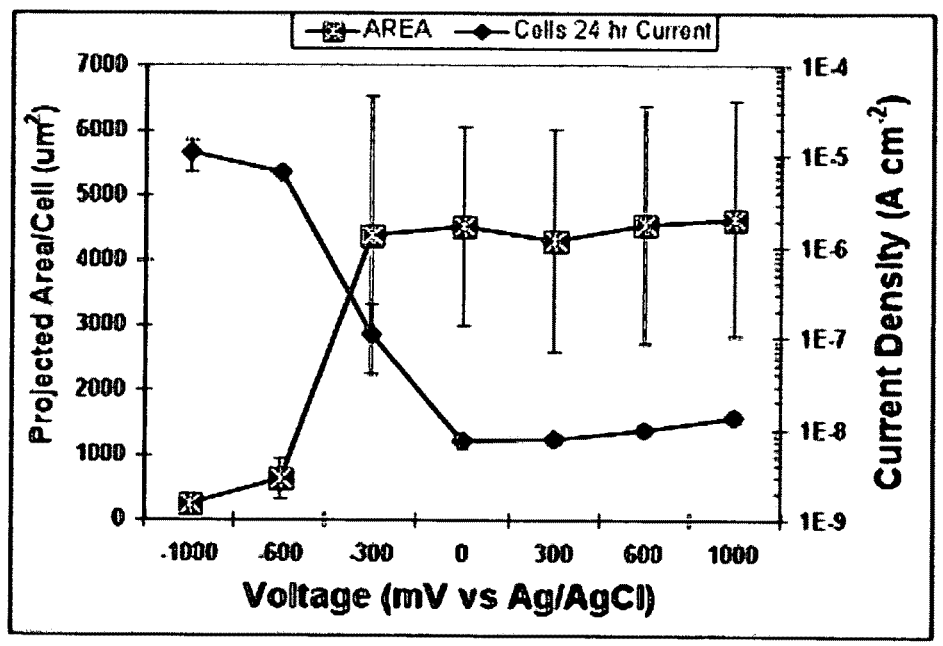
FIG. 14B depicts MTT cell viability results and polarization resistance measurements of the interface versus potential.

The results seen in FIGS. 14A & 14B clearly show that there are relationships between the surface behavior (cathodic current density levels and polarization resistance levels), and cell viability. Another important observation in these results is the fact that the surface oxide of titanium changes its resistance to charge transfer with voltage and that below about 0 mV vs (Ag/AgCl), there is a significant (several orders of magnitude) change in the polarization resistance of the material. Thus, net cathodic currents transiting the interface are likely altering the semiconducting character of the Ti-oxide making it easier to transport charge across the interface.

These results demonstrate a couple of important points. First, it is possible to study the role of electrochemical potential on the behavior of cells cultured on metallic alloy surfaces and correlate their behavior with electrochemical properties of the interface. Second, the oxide of titanium is susceptible to changes in response to potentiostatic control of its surface. Specifically, the polarization resistance of the interface decreases by orders of magnitude in response to cathodic excursions in voltage. Third, cells cultured on these surfaces are susceptible to significant changes in behavior over the voltage range studied. In particular, cell viability drops when the static potential is held somewhere below −300 mV vs Ag/AgCl for 24 hours.

These results all support the idea that if one can control the voltage of the implant that there are strong effects on cell behavior. The results seen are basically an ability to disrupt the living systems of the cell with cathodic bias when the cell is directly in contact with the surface. The effects are very pronounced with only slight excursions in voltage away from resting voltages giving rise to pronounced effects in terms of cellular response.

This, of course, raises questions about how these results relate to cathodic DC electrical stimulation of bone formation. The differences between this model and the DC stimulators are that this is a cell culture environment with the cells cultured directly on the titanium surface, whereas DC electrical stimulation takes place inside a living species, in the vicinity of the electrode implanted adjacent to bone. This implies that the stimulatory effects of cathodic bias may be greater in slightly remote locations to the metal surface, whereas cells in immediate contact with the surface will experience much greater adverse effects.

The extent of voltage excursion (and the associated changes in current density and surface impedance properties) is relatively small. It only requires current densities in the range of 100 nA/cm2 to induce the effects seen with voltages dropping only a few 100 millivolts from the resting OCP of the alloy over 24 hours. Titanium and its alloys tend to have open circuit potentials (OCP) in the range of −100 to −300 mV vs Ag/AgCl. Thus, when the voltage is dropped only 300 mV a nearly 80% decrease in cell viability is observed.

Another element of the observations is that if these mammalian cells exhibit such strong adverse reactions to these voltage excursions, then these voltages may well influence other cells. For instance, bacterial colonization of implant surfaces results in bacterial cells attaching directly to the implant surface. If these cathodic currents can induce cell death in bacterial cells by disrupting the multiple basic mechanics of life, then it is likely that this approach will be a strong approach to inhibiting early implant-centered infection of metallic medical devices. Also, macrophages are known to be able to withstand greater ranges of environmental conditions before undergoing programmed cell death or necrosis, so it is likely that a macrophage cell line (which is likely to be present in the early stages of implantation) may exhibit significantly different responses to these voltage excursions than MC3T3 cells.

Electrochemical Control of Biological Interactions at the Metallic Biomaterial Interface: Fibrinogen Adsorption Interactions Experiments to explore fibrinogen (Fb) adsorption were performed on 316L Stainless Steel coupons. These coupons were electrochemically polished to obtain near-atomically flat surface upon which the fibrinogen molecules could be directly observed with atomic force microscopy (AFM). The polishing method, reported in Sawyer, P. N., Electrode-Biological Tissue Interreactions at interfaces—a Review. Biomaterials, Medical Devices, and Artificial Organs, 1985. 12(3-4): p. 161-96, is one that is similar to commercial methods to prepare vascular stent surfaces. Solutions of fibrinogen in phosphate buffered saline solution were prepared to yield concentrations of Fb concentrations on the order of 1 to 5 ug/ml.

Two types of experiments were performed: ex-situ and in-situ. In the ex-situ experiments, the steel coupons were held at fixed voltage (range −500 to +600 mV) using a potentiostat (Pine Instruments AFRD-3) and immersed in the protein containing solution for fixed periods of time (ranging up to 60 minutes). Afterwards, the samples were carefully removed, rinsed, dried and examined with AFM (Digital Instruments Nanoscope IIIa) using tapping mode in air.

In the in-situ experiments, the tapping mode fluid cell of the AFM was adapted to allow for electrochemical control of the steel surface while imaging, and the protein containing solution was flowed over the surface. In this way, the time-based changes in protein attachment could be directly observed. Protein coverage, as an area fraction, was determined using bearing analysis (part of the AFM software) and the area fraction versus time was collected for up to 60 minutes. Also, protein height above the surface was determined using section analysis methods (also part of the AFM software). This has been detailed in Srinivasan, S. and Sawyer, P. N., Role of Surface Charge of the Blood Vessel Wall, Blood Cells, and Prosthetic Materials in Intravascular Thrombosis. Journal of Colloid and Interface Science, 1970. 32(3): p. 456-63.

Figure 15A:
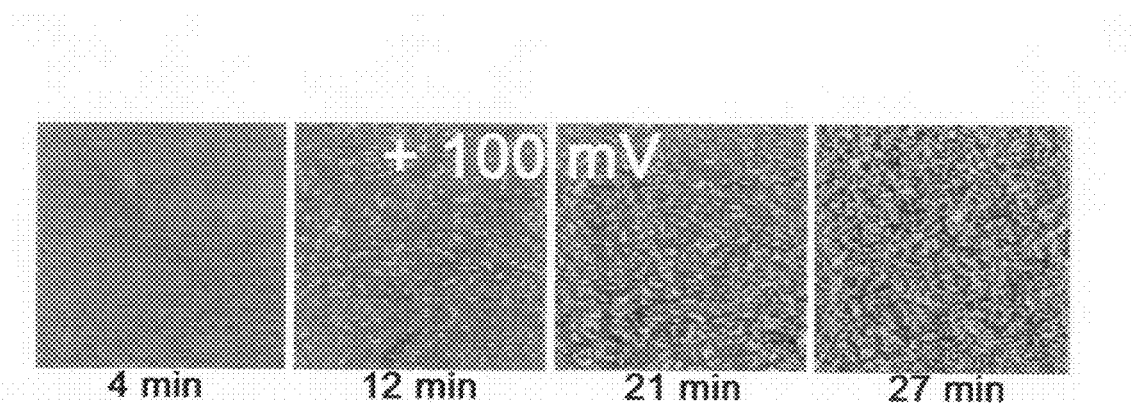
FIG. 15A shows time-sequenced AFM images of Fb adsorbing to 316L Stainless Steel at +100 mV.
Figure 15B:
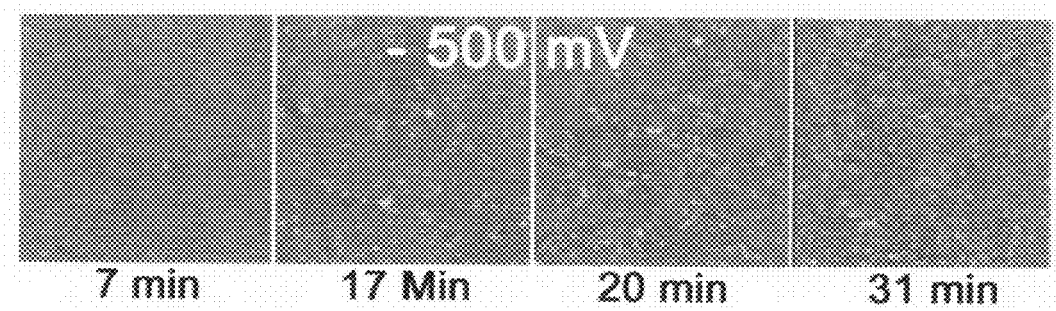
FIG. 15B shows time-sequenced AFM images of Fb adsorbing to 316L Stainless Steel at −500 mV.

The results of Fb adsorption onto stainless steel are shown in FIGS. 15A and 15B. Atomic force microscopy (AFM) images from in-situ tests at two different voltages (−500 and +100 mV) are shown. Here, adsorption from a 5 ug/ml Fb/PBS solution was performed in real time. It can be seen, for example, that individual protein molecules, somewhat randomly distributed, appear on the surfaces of these samples after about 12 to 17 minutes, but that the number of molecules seen at −500 mV is much less than that seen at 100 mV (at a shorter time). Also, the progression of adsorption can be observed with a high level of protein coverage present for the 100 mV sample at 27 min, whereas the −500 mV surface shows much less protein coverage.

Figure 16:
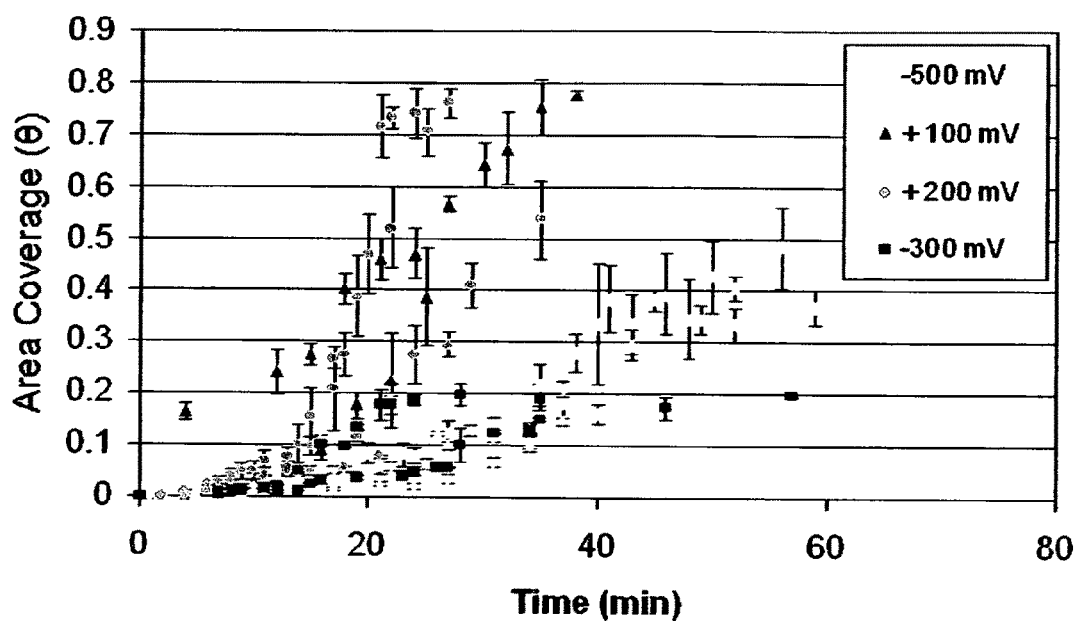
FIG. 16 depicts the kinetics of 5.0 ug/ml Fb adsorption onto electrically polarized 316L SS.

These results were quantified and the area fraction covered by Fb versus time, for different voltages are summarized in FIG. 16. Here, the adsorption behavior appears to follow a sigmoidal time dependence. The early lag in the adsorption is due to the nature of the experiment where prior to introducing the protein solution, only PBS was flowing.

It takes several minutes (up to about 7 to 10 min) before protein reaches the AFM fluid cell. Then, there is a rise in the coverage with time. There is a clear voltage dependence, where more cathodic potentials slow the rate of adsorption.

Figure 17A:
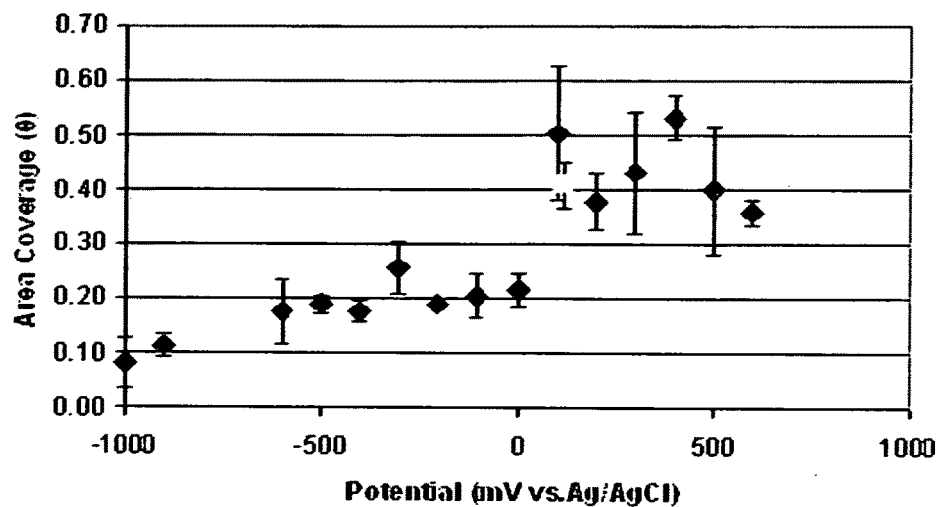
FIG. 17A shows protein area coverage of polarized 316L SS.
Figure 17B:
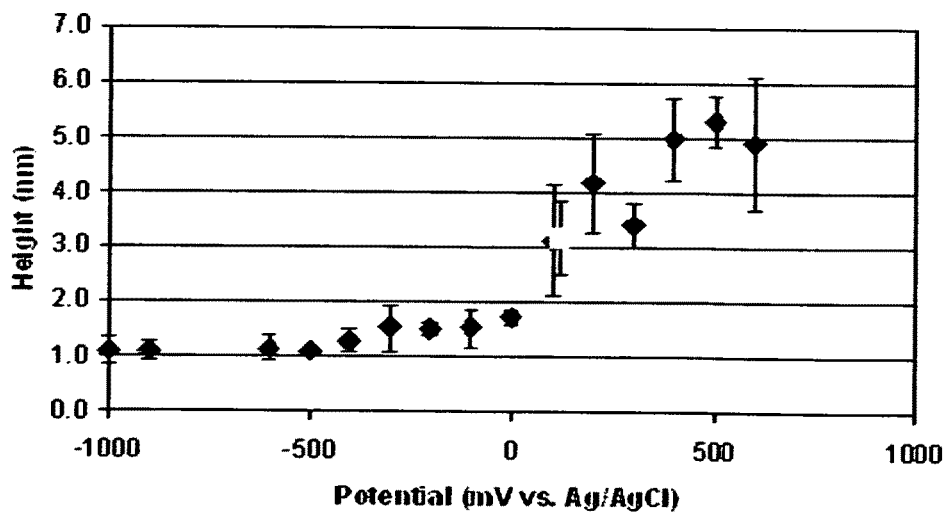
FIG. 17B shows protein height of polarized 316L SS.

From the ex-situ experiments, the coverage, after a fixed period of time (30 minutes) at different voltages, and the average height of the protein was quantified and are reported in FIGS. 17A & 17B. The coverage shows a trend of increasing with potential from very negative potentials, with a significant increase occurring around 0 mV. At the most anodic potentials, the coverage appears to level out. Similarly, the height of the protein layer starts out very low, about 1 nm and increases with potential, with a large increase taking place around 0 mV.

The major goal of these studies is to explore the effects of electrochemical voltage on protein-surface and cell-surface interactions. It is clear from this work that both fibrinogen adsorption and shape, and cell attachment, spreading and behavior are influenced by the applied voltage. These effects are not only related to electrostatic charge effects, but are likely affected by the electrochemical currents generated at metal surfaces when they are held at specific potentials. For instance, when both Ti or 316L stainless steel are held at cathodic potentials, reduction reactions, typically related to oxygen reduction, or water reduction will take place. The byproduct of these reactions is reduced oxygen and increased hydroxide ion, thus pH shifts are possible (see Smith, I. O., Baumann, M. J., and McCabe, L. R., Electrostatic Interactions as a Predictor for Osteoblast Attachment to Biomaterials. Journal of Biomedical Materials Research, Part A, 2004. 70: p. 436-441). Faradaic currents at the surface also act to dramatically increase the distance from the surface of these metals where electric fields can be sensed by the biological system. That is, the typical view of the electrified interface (from standard theories) is that of a diffuse electrical double layer and perhaps a specifically adsorbed charge layer (i.e., Stem Layer). These charge layers, which result from electrostatic interactions, are thought to effectively shield the biological solution out beyond a few nanometers from the surface from any electric fields resulting from charge at the surface. However, when Faradiac currents (electrochemical currents) are present, then the flux of charge away from the surface necessarily creates an electric field that penetrates much farther into the solution and this field may alter the nature of the interactions present. The concept of Faradaic currents altering the electrical double layer has not been explored in the context of biological-metal surface interactions.

The protein adsorption results generally support the early work of Sawyer (see Sawyer, P. N., The Relationship Between Surface Charge (Potential Characteristics) of the Vascular Interface and Thrombosis. Annals of the New York Academy of Sciences, 1983. 416: p. 561-83), who showed that the potential of a metal surface will affect the thrombogenicity of the surface where noble metals (Au, Pt) will quickly induce thrombus formation, and active metals (Cu, etc.) will inhibit clotting.

It is also important to note that in embryonic development, large electric fields are developed by the embryo and these fields are thought to be very important in guiding the development of structures, organs and limbs. Furthermore, many of the biochemicals associated with inflammation (as well as other systems in the body) are redox-based systems. Reactive oxygen species byproducts (e.g., hydrogen peroxide) are known to be electrochemically reduced at cathodic potentials (see Kotwal, A. and Schmidt, C. E., Electrical Stimulation Alters Protein Adsorption and Nerve Cell Interactions with Electrically Conducting Biomaterials. Biomaterials, 2001(22): p. 1055-1064). Thus, the voltage of a metal and the associated Faradaic reactions may result in effects at preventing inflammation.

Effect of Mg/Ti Area Ratio on the Potential and Current Densities at the Ti Surface The invention uses Mg, coupled to a titanium implant (or other alloy) to manipulate the potential of the implant to induce changes in the biological system's response to the implant. That is, the effects observed in the above section where cathodic potentials on the titanium surface (applied by an external power source) have affected cell responses, should be repeatable on Ti surfaces that have their cathodic bias controlled by another metal whose OCP is much more negative and who will act to pull the OCP of the Ti surface down into the range where effects are demonstrated. Here, the Mg will act as a sacrificial anode, undergoing high rates of corrosion, while the Ti will act as the cathode, where reduction reactions, similar to those seen above, will be present.

Figure 18:
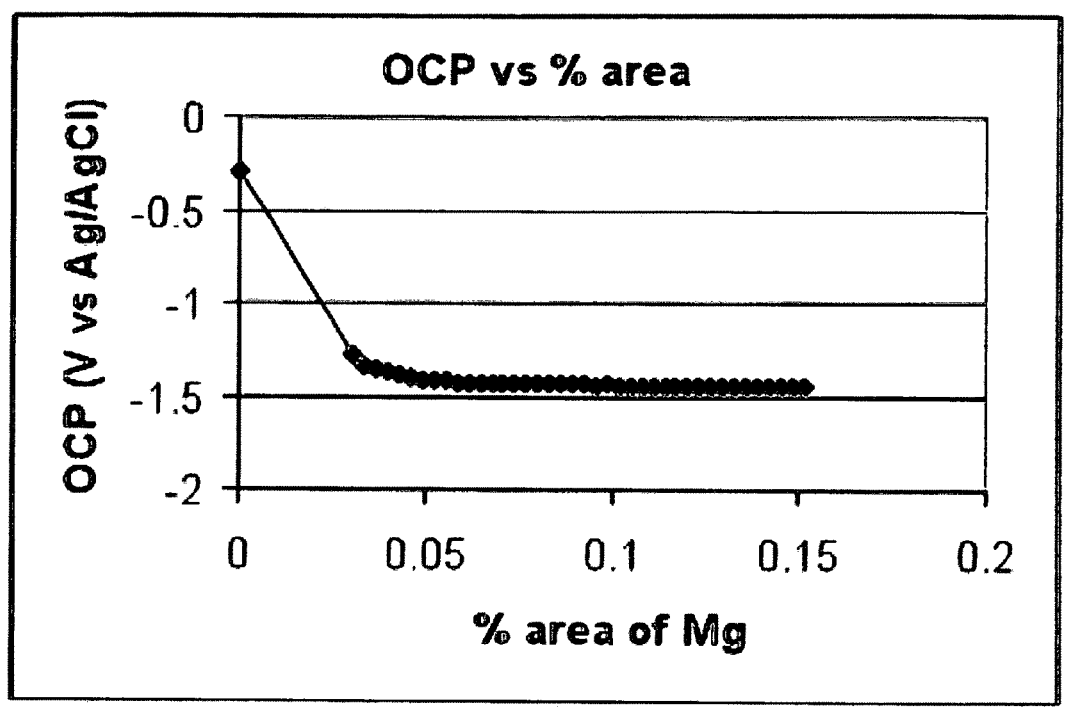
FIG. 18 depicts area ratios (given as a percent of total area as Mg) as a function of the overall voltage of the combined electrode system.
Figure 19:
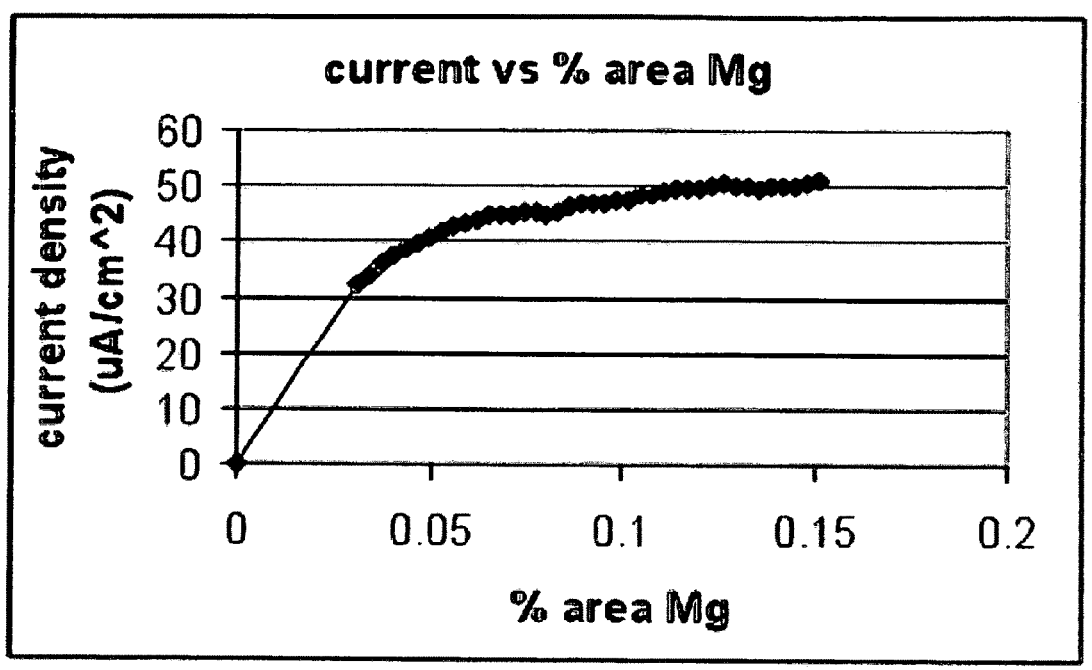
FIG. 19 depicts cathodic current densities passing the Ti surface as a function of the ratio of Mg to Ti (given as a percent of area as Mg) according to the invention.

The results of one such test is shown in FIGS. 18 and 19. FIG. 18 shows how the open circuit potential (OCP) of the combined system is affected by the coupling of Mg to Ti. With no Mg immersed, the voltage of the Ti is around −300 mV vs Ag/AgCl, when the Mg is first immersed at the smallest area fraction (0.03% Mg), the voltage of the combined system dropped almost −1 V (from −300 mV to about −1.3 V). As the amount of Mg immersed increased, the overall potential continued to decrease to about −1.5 V. The OCP of the Mg alone in PBS is about −1.6 V vs Ag/AgCl. FIG. 19 shows the current density developed by the coupling of the Mg to the Ti. It can be seen here that when there is no Mg attached, no current flows and that with the smallest Mg in solution, the current densities at the Ti surface increase dramatically at low percent Mg areas, and then continue to increase more slowly as the percent area Mg increases up to 0.15%. Note the current density presented is the total current flowing between Mg and Ti, divided by the area of Ti immersed and will be a cathodic current at the Ti. On the other hand, the current density at the Mg surface will be anodic, indicating oxidation, or corrosion, of the Mg and will be at a much higher current density (see FIG. 20A). Interestingly, the anodic current densities at the Mg surface are on the order of 10 to 100 mA/cm2 and they decrease with decreasing voltage (towards the −1.6V ranges which is the OCP of the Mg alone.

Figure 20A:
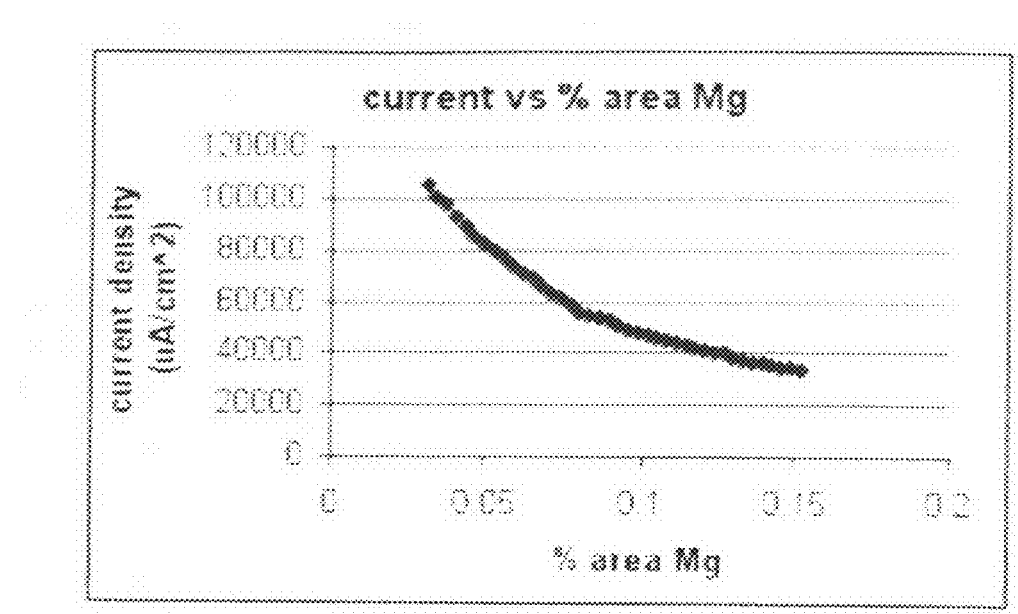
FIG. 20A depicts anodic current densities passing the Mg surface when coupled with CpTi, indicating a high rate of corrosion of the Mg.

FIG. 20A shows that exceedingly small areas of Mg, when coupled with Ti will pull the voltage of the entire electrode system very negative and that the rate of corrosion of the Mg will be very high, while the cathodic current densities will be well above the 100 nA/cm$^2$ range seen in the cell culture experiments to cause effects on the osteoblast cells. It appears that Mg is very effective in terms of its abilities to pull the voltage of the system into the cathodic range. Even the smallest amounts of Mg immersed into solution causes at least −1V drops. Alternative anodes may have less severe voltage excursions and greater control of the surface voltage. These metals include zinc and iron, both of which are tolerated by the body in ionic form and which will have a less negative OCP and corrosion kinetics.

Figure 20B:
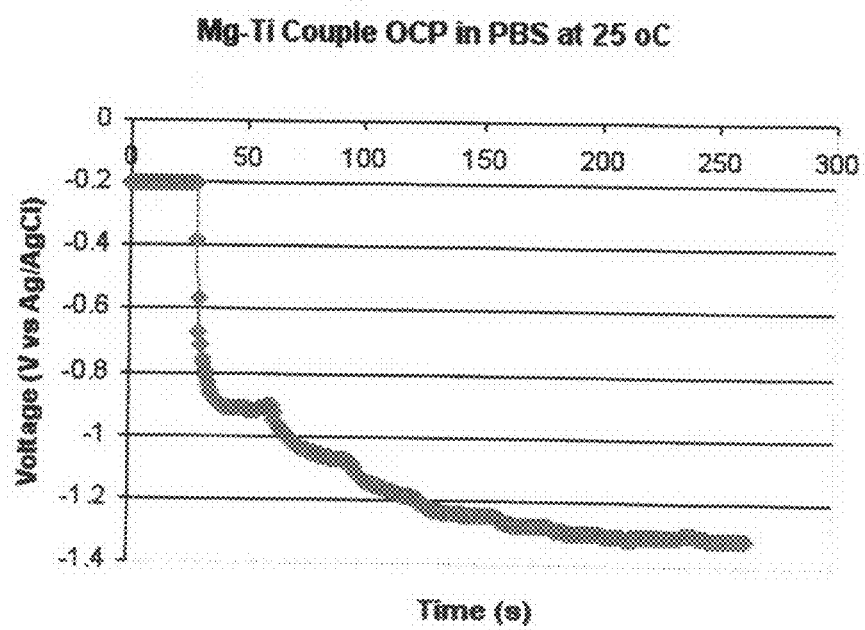
FIG. 20B depicts OCP versus time for Ti-6Al-4V/AZ31 alloy couples in PBS with incremental additions of Mg wire (AZ31 alloy) into solution.

FIG. 20B shows Open Circuit Potential (OCP) of Ti—Mg couples as a function of time as the amount of Mg in solution is incrementally increased. Ag/AgCl reference electrode was a Ti-6Al-4V cylinder 65.5 mm length and 25/2 mm diameter which was immersed in PBS. 0.8 mm diameter AZ31 Mg wire was immersed to increasing depths (8 steps up to 14 mm into the solution). OCP was allowed to equilibrate and then values were read from graph. Area fraction of Mg to Ti was determined and OCP vs area fraction was determined. Short time intervals were used between depths (on the order of 30 seconds). Steps in voltage indicate a subsequent advancing of the Mg into solution. Initial OCP is for Ti-6Al-4V alone in Phosphate Buffered Saline. The first small addition of Mg wire produced a negative excursion to about −900 mV. Increased fractions of Mg wire into solution increased the potential drop to as low as −1.3 V.

In tests over time, decreased OCP levels can be sustained for up to 3 to 4 days when Mg wire is embedded into the Ti surface by drilling a hole and pushing the wire into the hole so that there is a significant depth of wire and controlled access of solution to only the top surface of the wire. Alternative methods of limiting exposure of the Mg to the solution are also contemplated (e.g., degradable polymer coating, alloying the Mg to provide more resistance to corrosion, etc.).

Figure 21:
FIG. 21 shows an SEM micrograph of Mg wire in Ti after 4 days of corrosion showing the corrosion products of the Mg attack (including Mg oxide needles and plates)

The Mg wire embedded into the Ti only allowed the outer most portion to be exposed to the solution while the inner most part remained electrically attached to the Ti. As the Mg wire corroded, corrosion products would accumulate at the outer portion of the hole and on the Ti surface as can be seen in FIG. 21. This image shows needles and plates of Mg-oxide that form on surface of the Ti adjacent to the hole where the Mg wire was placed. It is clear that the Mg wire corrodes very rapidly and results in solid degradation products around the site where the Mg had been.

Figure 22:
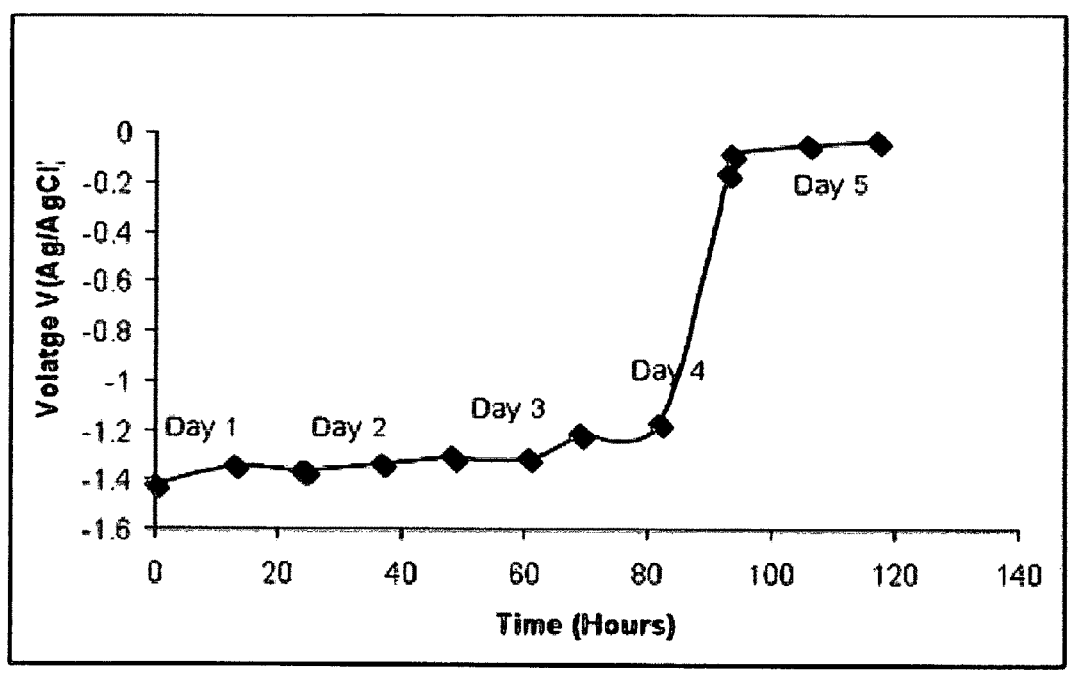
FIG. 22 depicts OCP versus time over 5 days for the Mg—Ti couples with Mg wire embedded in a hole in the Ti surface.

Additional experiments were performed to assess the long-term OCP response to couples of Mg and Ti. Mg wire was either pressed into a hole in the surface of the Ti sample, or they were held in an embedding medium to limit fluid access to the wire and the voltage (OCP) was monitored over 5 days. A typical result from one such test is shown in FIG. 22. The OCP remained cathodic for about 4 to 5 days after which the Mg was completely corroded and the OCP recovered to the Ti levels.

Cell Culture on Ti in the Presence of Mg Wires: 24 hr Exposure and 2, 4, 6 Hour Exposure Experiments In a next series of experiments, Mg wire was coupled to Titanium disk electrodes and bone cells were cultured on the surface for 24 hours. As a control, similar cell numbers were cultured under the same conditions but on Ti disks with no Mg wire. These so-called OCP samples were used to assure that the methods and particular cell population used would result in attached and spread cells in the absence of the Mg. Mg wires were not directly embedded in the Ti, but rather were held in the solution off to the side so that the corrosion debris would not obscure the cells afterwards.

Figure 23:
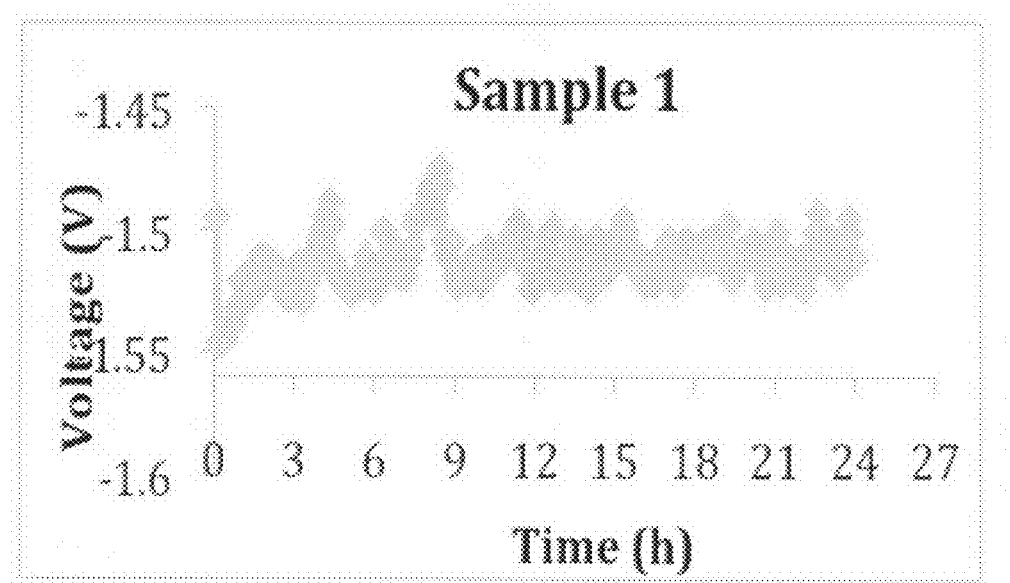
FIG. 23 depicts OCP versus time for Mg—Ti couple in cell culture.

Cell morphology was assessed after 24 hours of exposure to Mg—Ti coupling and compared to Ti at its resting OCP. The short-term response of MC3T3 cells to Mg—Ti coupling was also determined. Cells were first plated on Ti and allowed to spread for 1 hour. Then, the Ti was coupled to Mg and the experiments were allowed to continue for 2, 4 or 6 hours The results of Mg—Ti coupling after 24 hours are summarized in FIG. 23, which shows how a typical OCP behaves over 24 hours of Mg—Ti coupling with cells attached. The voltage remains within about 50 mV of −1.5 V over the entire time period.

Figure 24A:
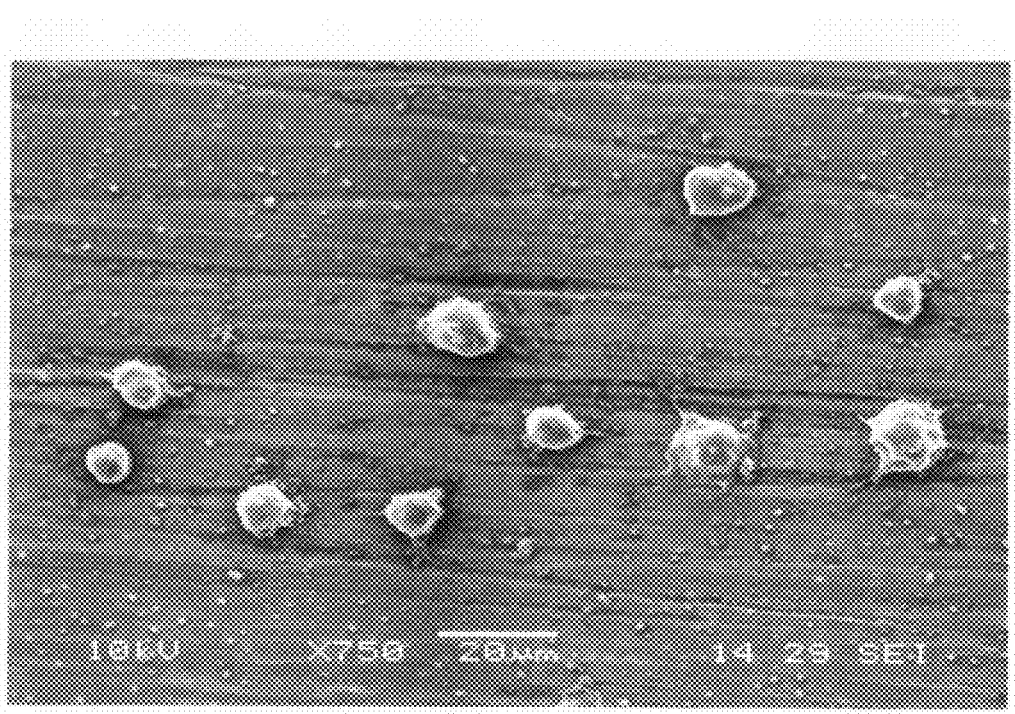
FIGS. 24A and 24B show SEM micrographs in (A) secondary electron imaging, and (B) backscattered imaging of cells on Ti coupled with Mg for 24 hr.
Figure 24B:
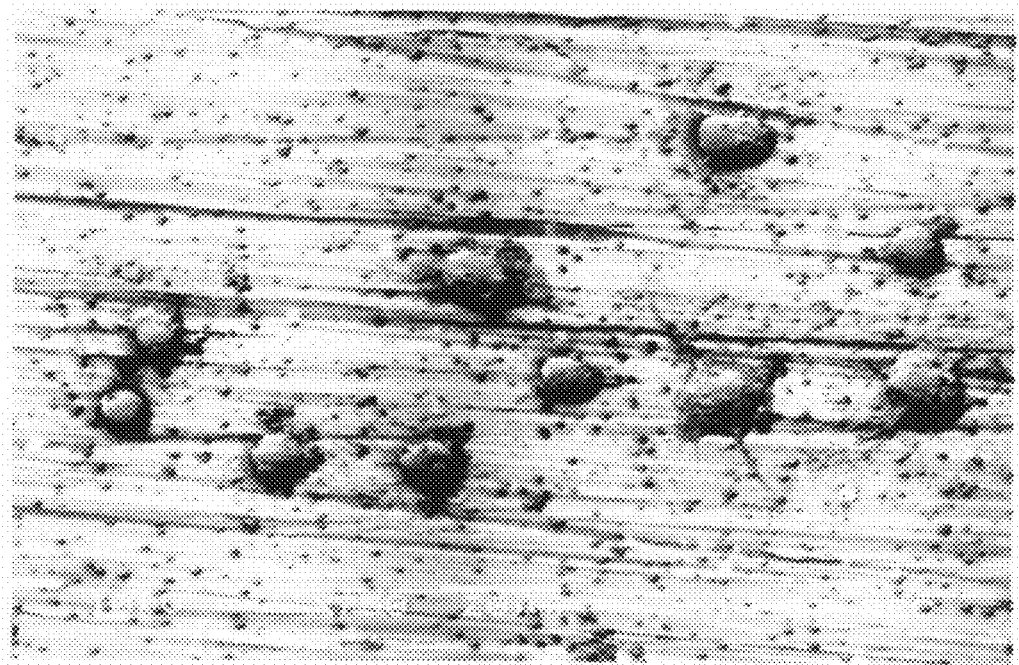
Figure 25A:
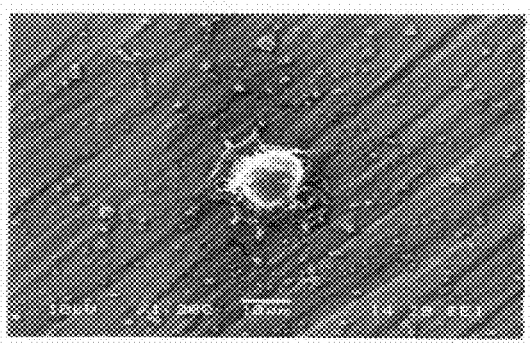
FIGS. 25A-D show SEM micrographs of cells after 24 hr coupled with Mg.
Figure 25B:
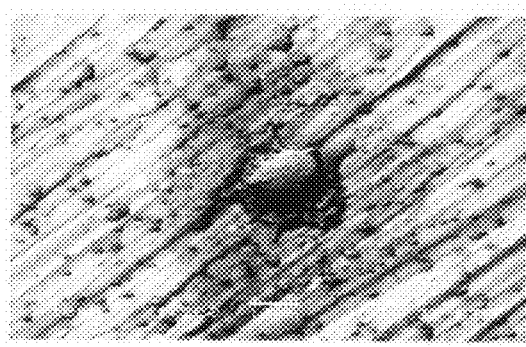
Figure 25C:
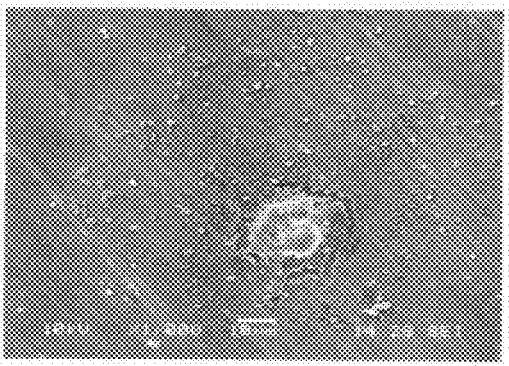
Figure 25D:
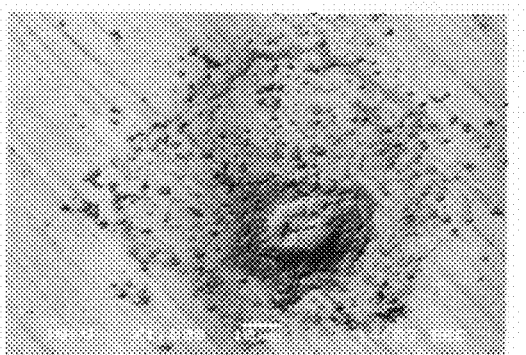

The cells cultured on Ti during coupling with Mg can be seen in FIGS. 24A and 24B. These are SEM images in secondary (FIG. 24A) and backscattered electron (FIG. 24B) imaging of the same region of cells after 24 hours, respectively. It should be noted that the cells in these experiments are similar in appearance to those held at −1000 mV in the earlier experiments. Also, there are remnant structures, seen in the backscattered images where the cells had spread and then either retracted or destroyed by electrochemistry. Debris in these regions appears to be evidence of the spreading extent that the cells reached prior to coupling.

FIGS. 25A-D show examples of high magnification images of cells culture on Ti after 24 coupling to Mg. Cell nuclei and the adjacent endoplasmic reticulum can be seen. Backscattered electron imaging (on right) gives an indication of the extent of the cell prior to degradation. The actin cytoskeletal structure appears degraded. The cells have contracted from a spread condition and are in distress or dead.

Figure 26:
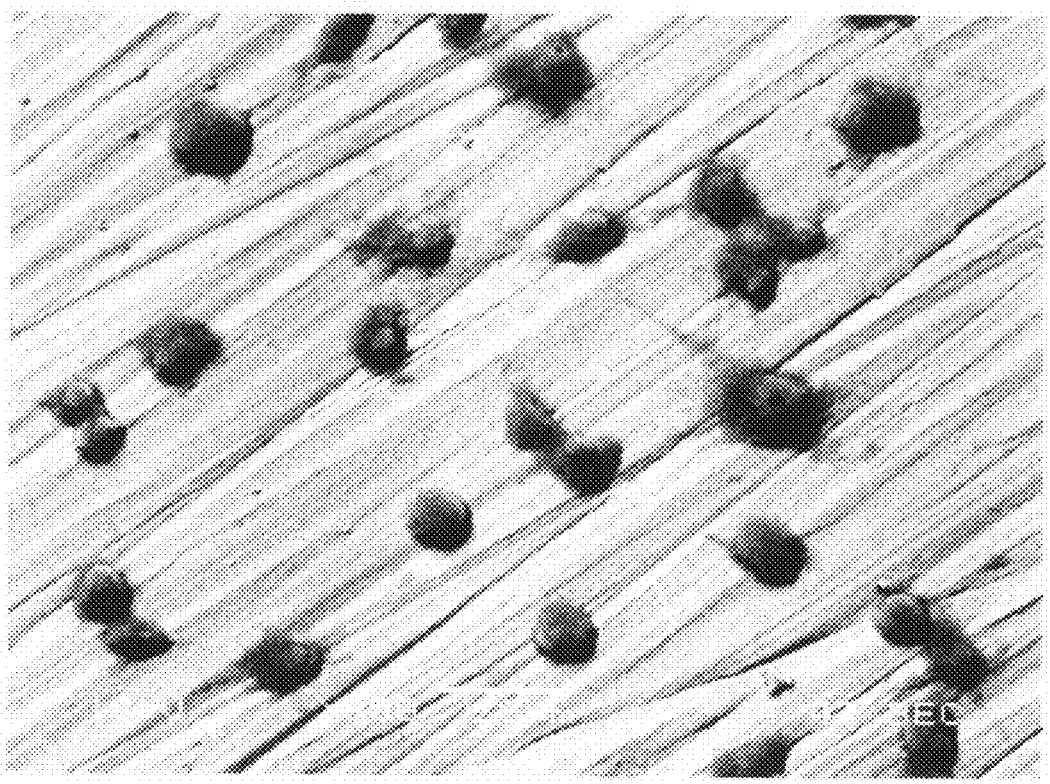
FIG. 26 shows SEM micrograph of a Ti surface after 24 hours of cell culture at −1300 mV.

As a control for the Mg—Ti couple experiments, additional tests were run on Ti alone potentiostatically held at −1300 to −1500 mV for different time periods to see if similar effects to Mg coupling were seen. An example of these results is shown in FIG. 26. Similar remnant cytoskeletal structures as in FIGS. 24A-B and 25A-D (Ti with Mg) are also seen when Ti is held at −1300 mV with cells. However, there were also cell bodies that were poorly spread evident on some regions indicating that the cells are not completely destroyed at this potential.

Cell Response Over Short Time Periods

The above experiments were performed over 24 hours to determine how cells respond to Ti—Mg coupling as well as holding the potential of Ti fixed in the absence of Mg. It was clear from these experiments that the cells are dramatically affected by a potential more negative than −300 mV for time periods of 24 hr. The next series of experiments explored how cell morphology changed over 2, 4 and 6 hours of exposure either to a fixed potential (−1000 mV) or Mg—Ti coupling. In the next section, the effect of potential over the range of −300 to −550 mV over 24 hr is explored to see how discrete or distributed the change in behavior is.

Figure 27A:
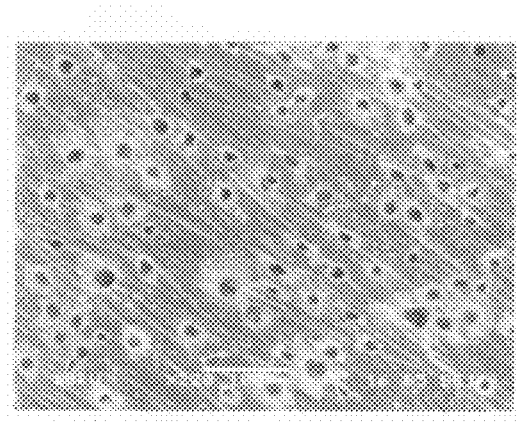
FIGS. 27A-27C show SEM Micrographs of MC3T3-E1 cells on Ti surfaces held at −1000 mV over (A) 2 hr, (B) 4 hr, and (C) 6 hr.
Figure 27B:
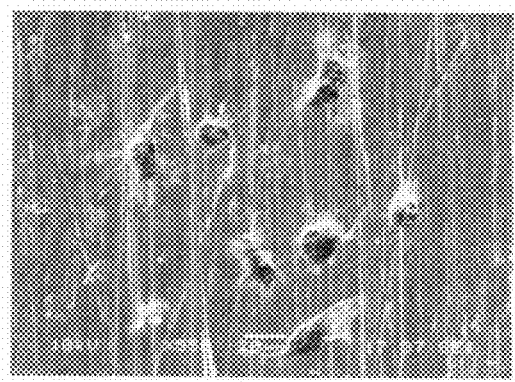
Figure 27C:
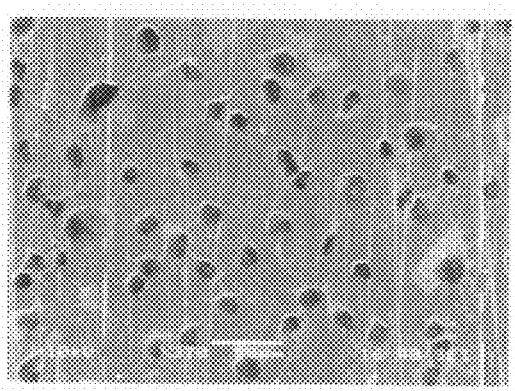
Figure 28A:
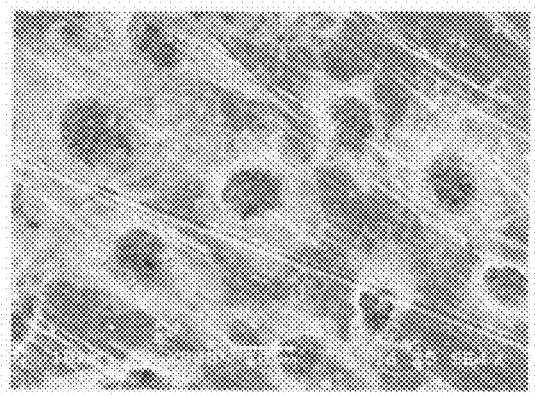
FIGS. 28A-28C show higher magnification SEM micrographs of MC3T3 cells in Ti at −1000 mV after (A) 2 hr, (B) 4 hr, and (C) 6 hr exposure.
Figure 28B:
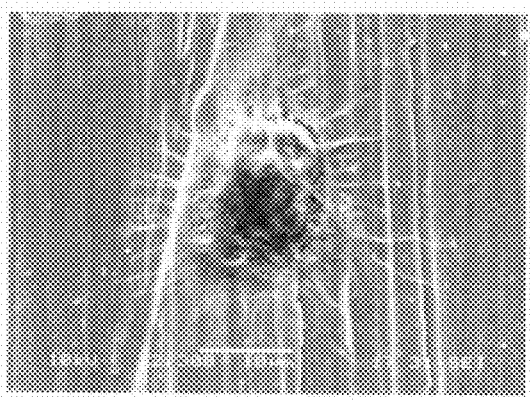
Figure 28C:
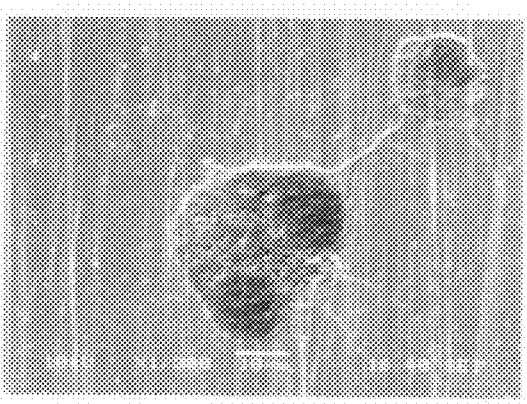

FIG. 27 summarizes −1000 mV exposure for 2, 4 and 6 hours, FIGS. 27A, B, and C, respectively. It can be seen from these representative micrographs that at 2 hr, the cells are engaged in cell attachment and spreading as might be expected on an OCP sample (note original magnification was 220× for FIG. 27A). However, by 4 hr, (FIG. 27B, 550×) the cells have retracted their cytoskeletal structures and the nuclei appear to be balling up and becoming more electron dense. The cytoskeletal structure has been broken down and the cell is consolidating around their nuclei. By 6 hr (FIG. 27C, 370×), the cells have undergone further retraction so that only the nuclei are apparent. Higher magnification SEM micrographs of these three time points at −1000 mV are shown in FIGS. 28A-C. These higher magnification images make clear the morphological differences in the cells after exposure to either Mg coupling or voltages below −600 mV.

Figure 29:
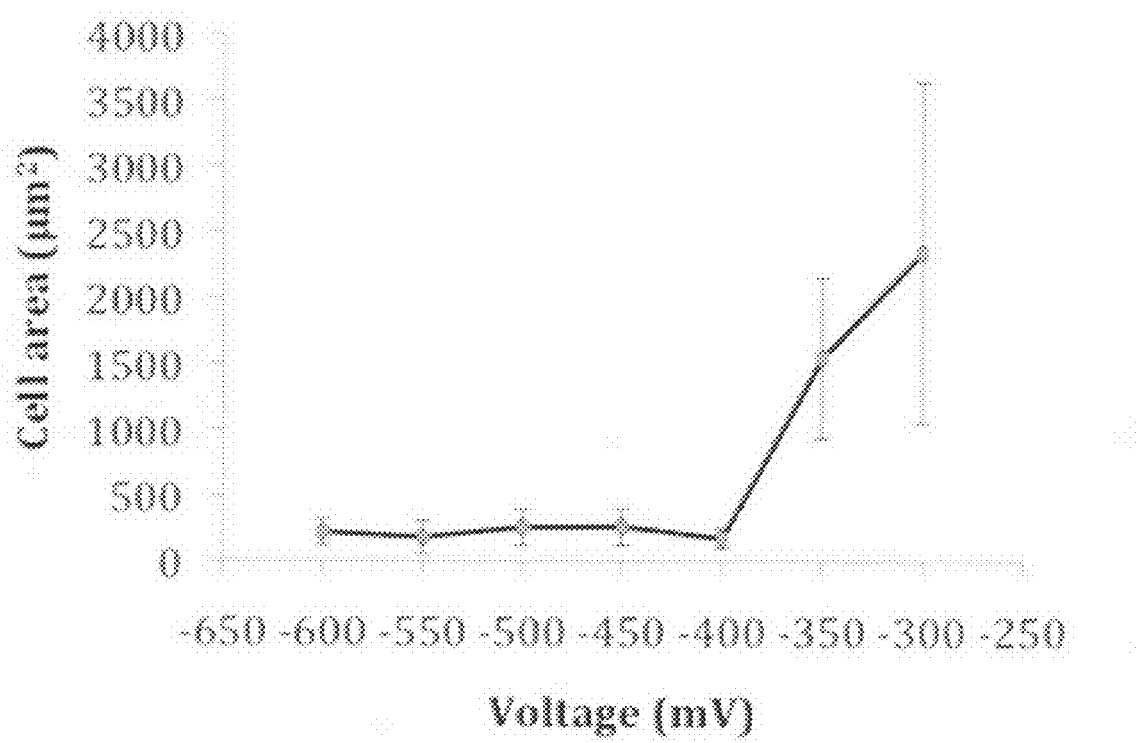
FIG. 29 shows a plot of cell area versus voltage after 24 hr exposure for the range of potentials from −300 to −600 mV in 50 mV increments.
Figure 30:
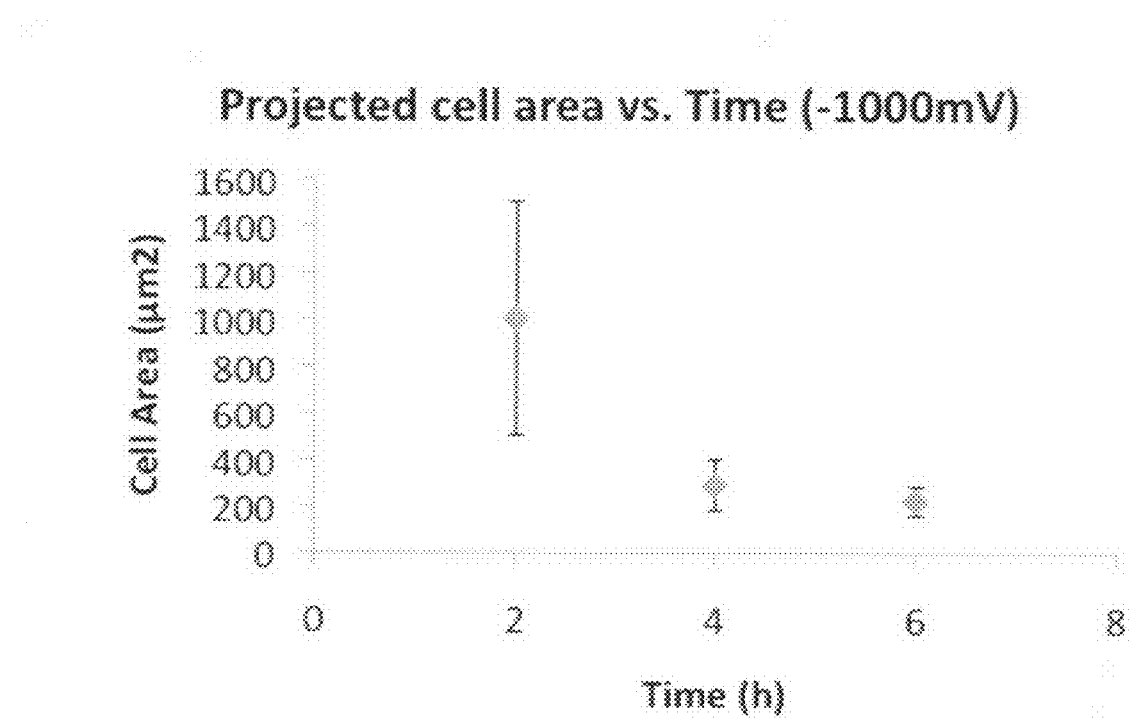
FIG. 30 depicts how cell area changes as a function of exposure time to −1000 mV.

The cell areas for these timed experiments were measured (mean and standard deviation), and are presented as a function of voltage (after 24 hr) in FIG. 29 and over time (at −1000 mV) in FIG. 27. FIG. 29 shows how the transition region between −300 and −600 mV and how small a range of voltage change is needed to induce the change in cell area. There are statistically significant changes in cell area from −300 to −400 mV. Most of the transition occurs between −300 mV and −400 mV. This 100 mV range is very small and represents a discrete transition in the character of the cells mostly related to the retraction of the cytoskeleton. FIG. 30 summarizes the time course changes in cell area when held at −1000 mV. The cellular shape change response occurs within about the first 4 hours of exposure to the potential (4 and 6 hr areas are statistically significantly different than the 2 hr area). This rate may likely be sensitive to the voltage relative to −300 mV since this appears to be the approximate voltage where the transition in behavior takes place.

Figure 31:
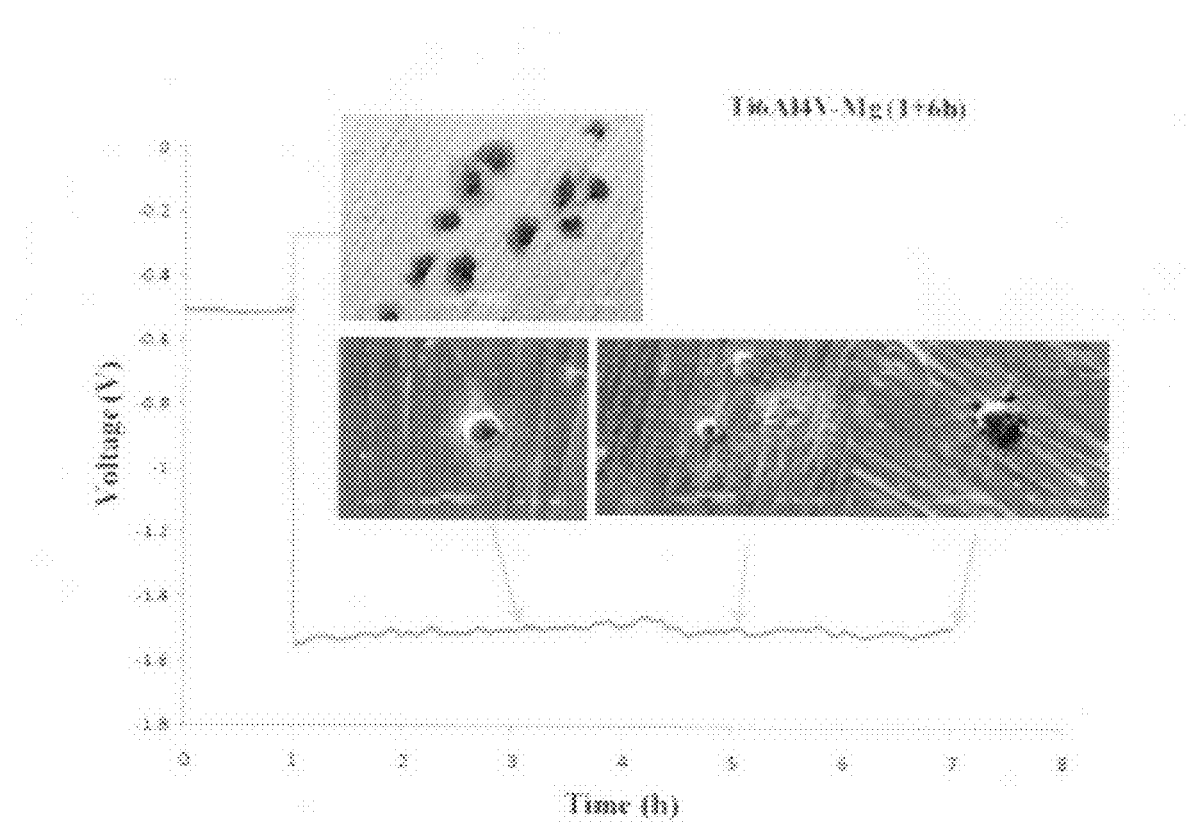
FIG. 31 depicts the effect of exposure time on cell area after coupling between Mg and Ti.

Similar time-dependent experiments were undertaken for Mg—Ti coupling over 2, 4 and 6 hr. The results of these experiments can be summarized in FIG. 31, which shows the OCP of the couple over time and the associated cell morphology at the identified time points. Note that in the first hr, no connection was made between the Mg and the Ti, hence the potential was more positive. Then, the Ti was connected to the Mg and the subsequent images show the cell morphology after these times of coupling. It should be noted that the 1 hr image is at a much lower magnification (350× original) compared to the other three (around 1900, 950, 1800 respectively).

One consistent observation in these studies is that the nucleus of these cells appears to undergo a morphological change from flattened at more positive voltages to rounded at more negative voltages. The SEM imaging, particularly in BSE mode allowed us to directly observe the intranuclear structures (nucleoli) in well spread and flattened cells (at positive potentials), and that the cell nuclei become more electron dense and rounded at more negative potentials.

Figure 32A:
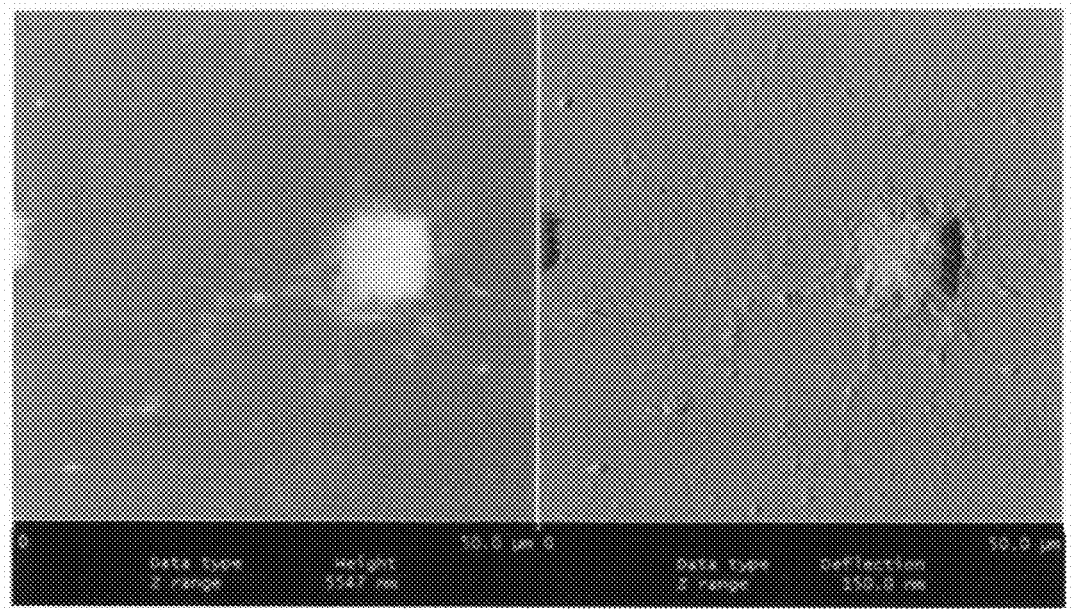
FIGS. 32A-32B show AFM height and deflection images of MC3T3 cells after 24 hrs culture (A) coupled to Mg (−1.5V OCP) and (B) at Ti OCP (about −300 mV)
Figure 32B:
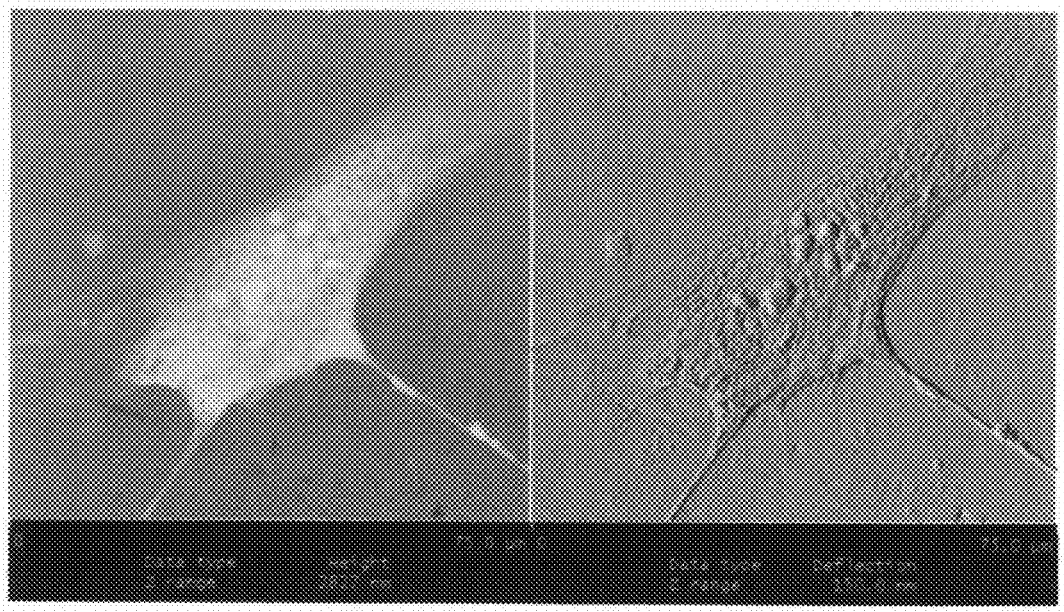
Figure 33:
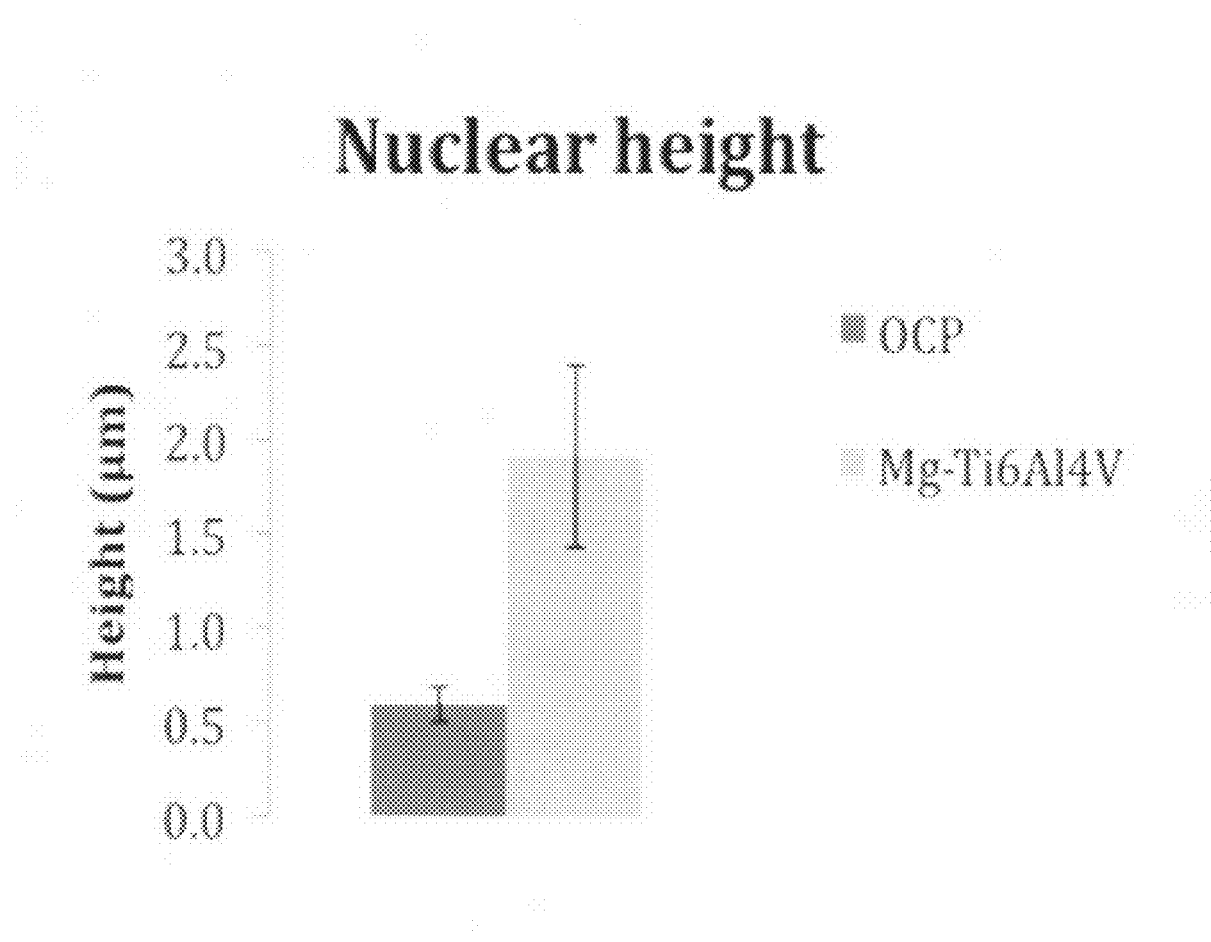
FIG. 33 shows the measurement of the heights of the nuclei of MC3T3-E1 cells cultured on Ti surfaces alone, or Mg-coupled Ti surfaces.

FIGS. 32A-B depict imaging of cells in the atomic force microscope (AFM) where permits direct measurement of nuclear height. Cells cultured on Ti at OCP for 24 hr and cells cultured on Ti coupled to Mg for 24 hr were placed into the AFM after fixing, dehydrating and drying. Prior to AFM imaging, the cell-surface samples were sputter coated with a thin layer of gold for later SEM analysis and then imaged in the AFM. Two examples of images are shown in FIG. 32. The effect of Mg coupling on intracellular structure is evident from these AFM images. In FIG. 32B, Ti OCP cultured cells have well defined nucleoli, endoplasmic reticulum and other cytoskeletal structures. The nucleus is flat and the cell is well spread. In contract, in FIG. 32A, cell culture on Mg-coupled Ti surface induced a breakdown of the cytoskeleton. The nucleus balled up and there is no evidence of nucleoli or other intracellular structures. Based on direct height measurement from the AFM images of the nuclei under these two conditions, the nucleus height was much flatter for the Ti-OCP cells compared to the Mg-coupled Ti cells. FIG. 33 summarizes the statistically significant increase in nuclear height on the coupled Ti surfaces (n=4).

Voltage has a Significant Effect on Cell Behavior Especially when the Potential Becomes More Cathodic.

The experimental results presented in this application demonstrate a very discrete transition in cell behavior between −300 and −450 mV. The coarse voltage work showed that cells cultured on surfaces above −300 mV up to +1000 mV showed little effect of voltage on the cell morphology or viability (see FIGS. 7 and 8). However, between −300 mV and −600 mV, at 24 hr, there was an 80% decrease in viability and cell area. This transition was further evaluated in 50 mV steps to show that the transition occurs between −300 and −400 mV primarily. This is less than 100 mV's and indicates that a fundamental transition in cell character is taking place (i.e., a molecular switch is thrown that leads to the cell retraction and death).

While the consequences to the cell in this experiment were not beneficial, this does not mean that a similar outcome will necessarily occur in-vivo. From work on DC electrical stimulation, cathodic potentials in-vivo provide a beneficial effect on bone healing in the vicinity of the electrode. Little work has been done to look at the direct interaction of cells and electrode surfaces when they have sustained potentials. It appears that when bone cells are in the vicinity of the electrode surface, these potentials are beneficial, however, cells cultured directly on the surface appear to be negatively affected.

This disparity in response seen between directly-cultured cells and cells in the tissue nearby to the electrode may be exploitable when it comes to infection control. Here, bacterial colonization of a metal implant surface requires the bacteria to attach directly to the implant (a so-called biomaterial-centered infection). If similar effects as those seen with mammalian cells, is seen with bacteria directly attached to the implant surface, then these bacteria may be killed by the voltage while the near-by bone may be positively stimulated with the same voltage range.

The coupling experiments show that a voltage drop in Ti can be induced by the presence of very small area fractions of Mg for periods up to 3 to 4 days. Only very small amounts of exposed Mg are needed to result in large drops in potential and relatively large levels of cathodic current densities. By embedding the Mg wire into a hole drilled into the Ti, the corrosion attack of the Mg can be slowed by restricting access of fluids to the Mg and thereby continuing the process for longer periods of time. It is possible that other methods of providing effective amounts of Mg in association with the Ti structure can be used as well. It should also be noted, that the byproducts of corrosion of Mg is the development of a hydrated Mg oxide precipitate that will form nearby to the Mg wire. These precipitates can grow and rearrange to result in large needle-like oxide structures, which may impact on how the biological tissues respond to the Mg.

The effect of Mg—Ti coupling on cell behavior is similar to that seen during application of potential alone. That is, similar cell morphology is seen (retracted cells) when the cells are cultured on Ti coupled with Mg. This indicates that the surface voltage, and the associated reduction reactions present are the key effect and not the Mg ions per se. The effects on cells occur over relatively short time periods of 4 to 6 hours after application of the voltage or coupling with Mg. Thus, the effects on the cells are rapid and voltage sensitive.

Figure 34:
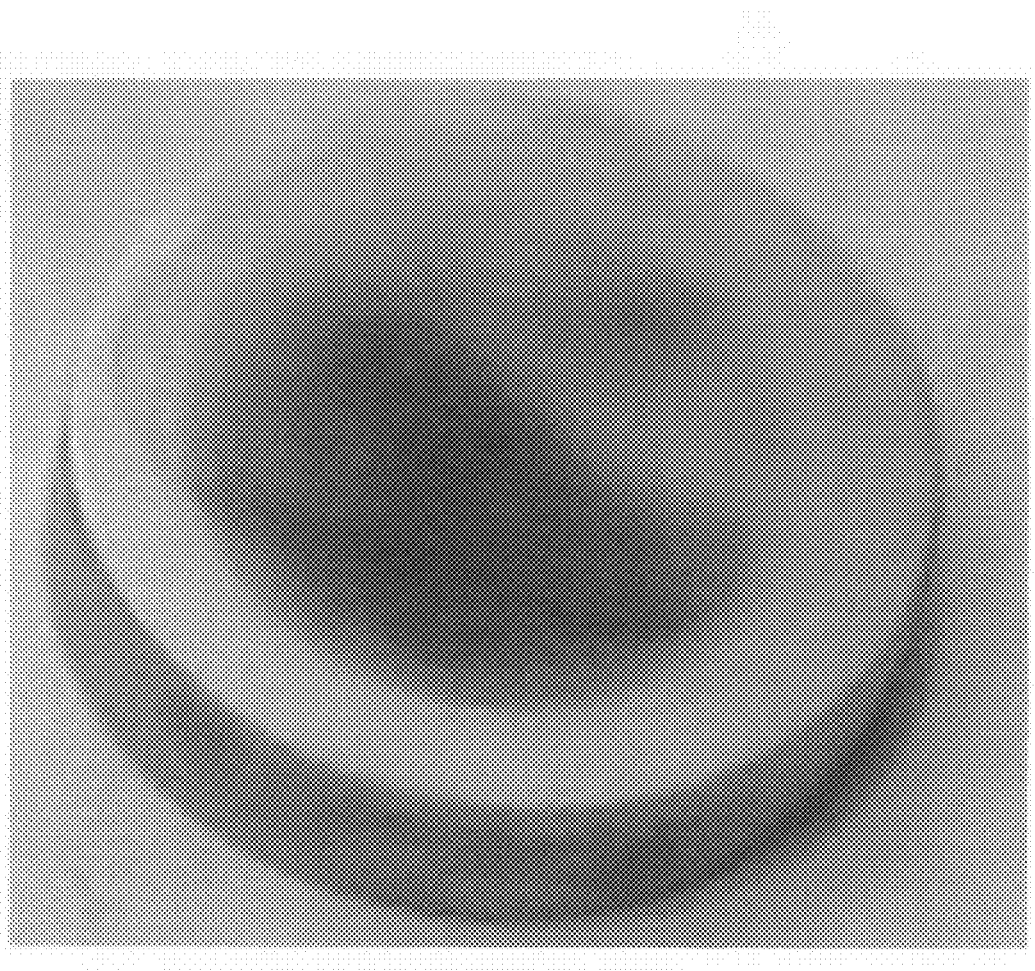
FIG. 34 depicts optical micrograph of Ti sample after 24 hr at −1000 mV in the cell culture system where the media was AMEM with FBS.

Cathodic voltage potentials may also change the local solution environment, for example oxygen and pH levels close to the surface of the implant or promote reactions with proteins, peptides and/or amino acids. There is some evidence for alteration of the proteins that interact with the surface of the Ti. This can be seen in FIG. 34, which shows the Ti surface after 24 hr exposure to the culture medium. The surface has been colored in a range of yellow to orange to green to blue on the surface when cathodically biased to −1000 mV. Lesser cathodic voltages (to about −600) also give this discoloration, although to a lesser degree than −1000 mV. Also, no colors are induced in Ti surfaces in the absence of the FBS or medium (i.e. in PBS). When there is no FBS in the medium there is still color, but it is much diminished. Many of the SEM and AFM micrographs of cells held at −600 mV or less showed large amounts of deposited protein and/or remnant cellular material. It is possible that redox processes are inducing alterations in the adsorbed proteins or amino acids and causing this discoloration to occur. Clearly, if the solution borne proteins are reacting with the surface of the implant, this too may affect cell response. Furthermore, other cell types, including macrophages which would be more likely to be present in the early post-operative period, may have a much different response to MC3T3 cells.

Mg—Ti Coupling in Biomedical Implants

An embodiment of the invention involves the use of a biodegradable implant metal, magnesium, as a tool for controlling the surface potential of titanium implants. Magnesium is a highly corroding metal in physiological solutions.

Its resting open circuit potential (OCP) is in the range of −1.6 to −2.0V (vs. AglAgCl), well below the normal potentials for implantable alloys like titanium, cobalt-chromium, etc. where resting OCP's are typically in the range of −0.3 to 0.1 V (vs. AglAgCl).

In an illustrative aspect, Mg wires (or other structures) are embedded into the surface of an implant in such a way as to control the overall potential of the surface for a period of up to 3 months. With an appropriate cathodic voltage developed by the presence of the Mg alloy material at the appropriate area ratio, bone in-growth may be enhanced and inflammation may be decreased at the titanium surface regions. The overall voltage established at a bi-metal surface (e.g., Mg—Ti alloy) will depend on the OCP's associated with each metal and the relative area of each present among other aspects related to the ease of various electrochemical reactions at these surfaces. Thus by controlling the relative amounts of Mg and Ti exposed, the voltage of the surface can be manipulated and controlled. According to an illustrative aspect, a particular voltage range can be provided at which the benefits of the Mg:Ti ratio will be optimized and enhanced rates of bone in-growth and minimization of inflammation can be developed.

Magnesium is proposed as a degradable implant alloy for use in cardiac and orthopedic applications. Most devices developed to date are utilizing Mg alloys for their ability to biodegrade. That is, they provide structural support for an initial period of time, but as corrosion progresses, the metal degrades away (via electrochemical reactions) until it is gone. A benefit of Mg is that the byproduct of its corrosion (Mg-oxide) is relatively harmless and, indeed, Mg ions are an important mineral used in biological systems. Thus while Mg can corrode readily, the bioburden of Mg is minimal and should not adversely impact the biocompatibility of the device.

According to an exemplary embodiment, Mg is used for regulating or controlling the overall surface voltage of a permanent medical device (at least for an initial period of time). These voltages may be used to induce specific biological processes that are beneficial to healing and integrating of the device.

Various exemplary aspects of the invention include:

Bi-metal combinations of Ti (or other implant alloy used in orthopedic or spinal applications for which rapid bone healing or minimization of infection or inflammation are required, e.g., Co—Cr—Mo, or 316L SS) and Mg with varying surface area ratios and volumes of Mg. The overall surface voltage will be affected by the relative exposed surface areas of, e.g., Ti to Mg. The Mg degrades over time and eventually the volume of Mg will be consumed (or encased in a passivating layer of corrosion products and tissue) leaving behind locations for bone in-growth. The electrochemical reaction of these surfaces with hydrogen peroxide and hypochlorous acid will depend on the voltage of the surface as well. The more negative the potential, the greater the driving force for reaction with these species.

It is expected that bi-metal combinations of Mg and Ti can be used to affect bacterial biofilms in the presence of antibiotics. It has been shown that when biofilms formed on implant surfaces are exposed to antibiotics alone, it is impossible to eradicate the infection. Currently, when an implant becomes infected, the only recourse is for the surgeon to remove the device, treat the local site with massive local antibiotics and, after the infection has resolved, return in a second operation to re-implant a new device. According to the aspect, a low DC field in combination with antibiotics will dramatically increases the ability to kill bacteria in biofilms on implant surfaces. The electrical potential (low DC field) can be provided in the form of a Mg alloy integrated into the implant surface, which will provide the electrochemical reactions needed to develop the low DC field.

Another embodiment provides voltage control of a medical device using Mg integrated into the device, and the use of electrochemically generated surface voltages to control: a) bone in-growth, b) reduction of inflammation, and c) attack of bacterial biofilms. This embodiment of the invention also pertains to development of orthopedic, spinal, dental, and other bone-interacting medical devices that can take advantage of this cathodic voltage control to manipulate bone healing, reduce inflammation and enhance resistance to infection.

Embodiments of the invention have numerous applications. Illustratively, the embodiments can be applied to a wide array of metallic medical devices. These include, but are not limited to, total joint replacements, where bone in-growth healing is important; fracture fixation devices used to bridge fractured bones and promote healing of the fracture; dental implants, where rapid bone in-growth is critical to long term success; spinal devices used to fuse spinal segments or otherwise create bone healing; and other applications where minimization of inflammation would be important, such as in cardiovascular stent coatings, for example.

Combination of Mg—Ti with Agonists of Bone Formation

Medical implants of the invention may also be treated using know methods to improve biocompatibility. For example, a number of surface modification techniques have been developed to enhance the corrosion performance and the wear resistance of Ti surgical implants alloys. Calcium phosphate ceramic materials may be used as coating materials that promote osseointegration. The most popular coating among the calcium phosphate family is hydroxyapatite (HA) due to its chemical stability and osteoconductivity. U.S. Pat. No. 4,908,030 discloses a method of forming a thin HA coating on an implant using ion beam sputtering. U.S. Pat. No. 5,817,326 discloses a method in which one or more layers of HA sol-gel are cured to density on a titanium alloy implant, followed by a non-line-of-sight ion implantation process, in order to strengthen the adhesion of the HA coating to the substrate. U.S. Pat. No. 5,543,019 discloses a method of forming a thin coating layer on the surface of an implant using a plasma sputtering process. Other methods developed include pulsed laser deposition, nitriding and magnetron sputtering. Additional coating methods are disclosed in U.S. Patent No. 7,341, 756, the contents of which are hereby incorporated herein in its entirety.

In other embodiments, the medical devices of the invention may be engineered to deliver drugs to the site of implantation according to methods known in the art. For example, the devices may be coated with a polymer material with cavities that are filled with drug loading vesicles of different sizes, whereby the larger cavities are filled first with larger vesicles (i.e. large vesicles are too big to fill the smaller cavities) and smaller cavities are later filled with smaller vesicles which will fill the remaining places available (i.e. in the small cavities remaining empty). Such a technique enables to store different drugs into the coating which may have different delivery profiles in time which may depend for example on the release properties of the vesicles selected (such as hydrophobic or hydrophilic properties; or polymer degradation properties).

In another embodiment, nanoparticles of biocompatible metal are combined (by coating, alloying, or colloidal interaction) with a cathodic-potential alloy (e.g., Mg) and covered with target cell-specific ligands. After implantation into a patient, the coupled nanoparticles specifically attach to the target cells and deliver lethal electrochemical stimulus thereby killing the cells. A target cell can include, but is not limited to, a cancer cell or a cell infected with a pathogenic virus or parasite. A ligand may be an antibody or other molecule having a binding affinity for an epitope at the cell surface of the target cell. Examples of monoclonal antibodies that bind specifically to antigens present on the surface of human breast cancer, human bladder cancer, and, human lung cancer cells are disclosed in U.S. Pat. No. 7,560,095. Examples of monoclonal antibodies directed to epitopes found on the surface of HTV infected cells are disclosed in U.S. Pat. No. 6241986. The contents of these patents are hereby incorporated herein in their entirety.

In other embodiments, Mg—Ti nanoparticles coated with cancer cell-specific monoclonal antibodies may be combined with more conventional cancer therapy, such as radiation and chemotherapy. For example, antibody coated Mg—Ti nanoparticles can be implanted in situ at the original site of a tumor that has been surgically removed. This approach can supplement existing seed implant therapy that is used to deliver localized radiation at the site of solid tumors (brachotherapy) or as part of image-guided radiation therapy (IGRT) protocols. Currently marketed radioactive seeds take the form of a capsule encapsulating a radioisotope. See, e.g., Symmetra® I-125 (Bebig GmbH, Germany); IoGold™ I-125 and IoGold™ Pd-103 (North American Scientific, Inc., Chatsworth, Calif.); Best® I-125 and Best Pd-103 (Best Industries, Springfield, Va.); Brachyseed® I-125 (Draximage, Inc., Canada); Intersource®I Pd-103 (International Brachytherapy, Belgium); Oncoseed® I-125 (Nycomed Amersham, UK); STM 1250 I-125 (Sourcetech Medical, Carol Stream, Ill.); Pharmaseed® I-125 (Syncor, Woodland Hills, Calif.); Prostaseed™ I-125 (Jrocor, Oklahoma City, Okla.); and I-plant® I-125 (Implant Sciences Wakefield, Mass.). The capsule of these seeds is made of a biocompatible substance such as titanium or stainless steel. Brachytherapy is further described in U.S. Pat. No. 6,746,661, the contents of which are hereby incorporated herein in their entirety.

In other embodiments, the medical implant may be coated with a nanotube or a nanowire scaffold that promotes more effective surfaces for hip replacement, dental reconstruction and vascular stenting. Medical devices comprising nanoparticles and/or nanocomposite materials are described in U.S. Pat. No. 7,517,353, the contents of which are hereby incorporated herein in its entirety.

Another particular type of implants that may be suited for Mg—Ti coupling are stents, which are used on diverse structures such as the oesophagus, trachea, or blood vessels. Prior to use, a stent is in general collapsed to a small diameter. When brought into place it is expanded using an inflatable balloon that is removed and is then held in place by its own tension against the surrounding tissue. Stents are usually inserted by endoscopy or other procedures less invasive than a surgical operation, which makes them also suitable for patients with advanced disease for whom an operation might be too dangerous. Stents may consist of wire mesh or other expandable structure alone, or may be coated by a suitable material.

In one embodiment, the medical devices with Mg—Ti coupling are coronary stent implants that are used for therapeutic cardiac procedures. Re-narrowing of a previously treated vascular lesion, termed restenosis, is considered the most important problem in interventional cardiovascular medicine. Stent placement has been shown to decrease the rate of restenosis. It involves placing a stent, which is a small mesh-like wire tube in a narrowed blood vessel. The stent holds the vessel open and helps reduce the rate of restenosis (a recurrence of the narrowing within the vessel). In general the vessel is an artery. Most of the implants (or at least a part of them) that are used today are made of bare-metal and/or polymeric material. Polymers are known to induce inflammatory responses which can translate into delayed healing and thus increased risk for an adverse outcome. Furthermore, bare-metal implants are also associated with side-effects. It has been shown that up to 40% of patients who received a bare-metal stent develop in-stent restenosis. The risk of adverse reactions or side effects can be reduced by additional administration of suitable drugs preventing the same. For this, implants releasing drugs which reduce adverse reactions or side effects have been developed.

For example, in-stent restenosis can be substantially reduced by the implantation of a drug-eluting stent (DES) (Babapulle et al., 2004, The Lancet 364: 583-591). Currently, two devices are approved by the FDA, both of which have shown efficacy towards the prevention of restenosis, the Cypher® stent (Cordis, Johnson&Johnson), which is coated with rapamycin (Moses et al., 2003, N Eng J Med 349:1315-1323) and the Taxus® stent (Boston Scientific) (Stone et al., 2004, N Engl J Med 350:221-231) that releases paclitaxel.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict between the present explicit disclosure and a document incorporated by reference, the present explicit disclosure shall be the operative disclosure.

What is claimed is:

1. A medical implant, comprising:
   a biocompatible material forming a surface for said implant;
   a metal having a cathodic electrochemical potential embedded in the biocompatible material and inducing a cathodic electrochemical potential at the surface of said implant relative to said biocompatible material in the absence of said metal.

2. The medical implant of claim 1, wherein said metal having a cathodic electrochemical potential comprises one or more members of the group consisting of magnesium, iron and zinc.

3. The medical implant of claim 1, wherein said metal having a cathodic electrochemical potential is disposed at the surface of said implant.

4. The medical implant of claim 3, wherein said metal having a cathodic electrochemical potential comprises less than 1% of the surface of said implant.

5. The medical implant of claim 1, wherein said biocompatible material comprises titanium.

6. The medical implant of claim 1, wherein said biocompatible material comprises an alloy.

7. The medical implant of claim 6, wherein said alloy is selected from the group consisting of titanium-aluminum-vanadium (Ti-6Al-4V), cobalt-chromium-molybdenum (Co—Cr—Mo), and stainless steel (316L SS).

8. The medical implant of claim 1, wherein said cathodic potential at the surface of said implant is configured to reduce an inflammatory response of a patient to said implant.

9. The medical implant of claim 1, wherein said cathodic potential at the surface of said implant is configured to inhibit bacterial proliferation on the surface of said implant after insertion of said implant into a patient.

10. The medical implant of claim 1, wherein said cathodic potential at the surface of said implant is configured to reduce or eliminate bacterial infection on the surface of said implant after insertion of said implant into a patient.

11. The medical implant of claim 1, wherein said cathodic potential at the surface of said implant is configured to promote bone healing at a site of insertion of said implant into a bone of a patient.

12. The medical implant of claim 1, wherein said cathodic potential at the surface of said implant is configured to promote a gradual corrosion of said metal having a cathodic electrochemical potential after insertion of said implant into a patient.

13. The medical implant of claim 1, wherein the surface of said implant further comprises an agonist of bone formation.

14. The medical implant of claim 13, wherein said agonist is selected from one or more members of the group consisting of osteoinductive growth factors, extracellular matrix constituents, scaffolding material, bone-specific enzymes and calcium phosphate particles.

15. The medical implant of claim 14, wherein said osteoinductive growth factors comprise a bone morphogenetic protein.

16. The medical implant of claim 14, wherein said scaffolding material comprises osteogenesis-inducing cells.

17. The medical implant of claim 1, wherein said implant is a stent.

18. The medical implant of claim 17, wherein said cathodic potential at the surface of said stent is configured to inhibit restenosis after insertion of said stent into a blood vessel of a patient.

* * * * *